United States Patent
Borkholder et al.

(10) Patent No.: US 10,561,341 B2
(45) Date of Patent: Feb. 18, 2020

(54) DEVICE PACKAGING FOR AN IMPACT DETECTION DEVICE

(71) Applicant: BlackBox Biometrics, Inc., Rochester, NY (US)

(72) Inventors: David A. Borkholder, Rochester, NY (US); Matthew Kenyon, Spencerport, NY (US); Ryan Ramplin, Rochester, NY (US); Michael H. Ostertag, Rochester, NY (US); Kim Sherman, Spencerport, NY (US); Matthew Wellman, Rochester, NY (US); Micah Harrison, Spencerport, NY (US)

(73) Assignee: BlackBox Biometrics, Inc., Rochester, NY (US)

( * ) Notice: Subject to any disclaimer, the term of this patent is extended or adjusted under 35 U.S.C. 154(b) by 377 days.

(21) Appl. No.: 15/268,259

(22) Filed: Sep. 16, 2016

(65) Prior Publication Data

US 2017/0065210 A1 Mar. 9, 2017

Related U.S. Application Data

(63) Continuation of application No. 14/248,849, filed on Apr. 9, 2014, now abandoned, which is a continuation
(Continued)

(51) Int. Cl.
*G01L 5/00* (2006.01)
*A61B 5/11* (2006.01)
(Continued)

(52) U.S. Cl.
CPC .............. *A61B 5/11* (2013.01); *A42B 3/046* (2013.01); *A61B 5/002* (2013.01); *A61B 5/4064* (2013.01);
(Continued)

(58) Field of Classification Search
CPC ....... A61B 5/11; A61B 5/6803; A61B 5/4064; A61B 5/002; A61B 2562/0219;
(Continued)

(56) References Cited

U.S. PATENT DOCUMENTS

| 4,392,830 A | 7/1983 | Salzman et al. |
| 4,440,160 A | 4/1984 | Fischell et al. |

(Continued)

FOREIGN PATENT DOCUMENTS

| WO | WO-2013109940 A2 | 7/2013 |
| WO | WO-2015021393 A1 | 2/2015 |

OTHER PUBLICATIONS

U.S. Appl. No. 14/140,613, Examiner Interview Summary dated Apr. 22, 2016, 3 pgs.
(Continued)

*Primary Examiner* — Xin Y Zhong
(74) *Attorney, Agent, or Firm* — Schwegman Lundberg & Woessner, P.A.

(57) ABSTRACT

An impact detection device for detecting impacts to a body part of a user and various supporting systems are discussed. In an example, an impact detect device can include a circuit board, a component having a first section and a second section, a battery, and a molding for housing the circuit boat, the battery and the component. The circuit board can include impact detection circuitry including at least two sensors and a communication circuit. A zone of reduced rigidity can connect the first and second sections of the component, with the circuit board secured to the first section. The battery can be secured to the second section of the component allowing for flex relative to the circuit board. The molding can be shaped and dimensioned for mounting to a body part of the user.

21 Claims, 30 Drawing Sheets

Related U.S. Application Data of application No. 14/140,613, filed on Dec. 26, 2013, now Pat. No. 9,380,961.

(60) Provisional application No. 61/863,555, filed on Aug. 8, 2013.

(51) Int. Cl.
*A61B 5/00* (2006.01)
*G01P 15/14* (2013.01)
*A63B 24/00* (2006.01)
*A42B 3/04* (2006.01)
*A63B 71/10* (2006.01)
*G01P 15/00* (2006.01)

(52) U.S. Cl.
CPC .......... *A61B 5/6803* (2013.01); *A63B 24/00* (2013.01); *A63B 71/10* (2013.01); *G01L 5/0052* (2013.01); *G01P 15/14* (2013.01); *A61B 2562/0219* (2013.01); *A63B 2220/53* (2013.01); *G01P 15/00* (2013.01)

(58) Field of Classification Search
CPC ..... A63B 71/10; A63B 24/00; A63B 2220/53; G01L 5/0052; A42B 3/046; G01P 15/14; G01P 15/00
See application file for complete search history.

(56) References Cited

U.S. PATENT DOCUMENTS

| | | | |
|---|---|---|---|
| 4,527,982 A | 7/1985 | Salzman et al. | |
| 5,539,935 A | 7/1996 | Rush, III | |
| 5,621,922 A | 4/1997 | Rush, III | |
| 5,869,761 A | 2/1999 | Nakamura | |
| 5,978,972 A | 11/1999 | Stewart et al. | |
| 6,053,045 A | 4/2000 | Nakamura | |
| 6,147,618 A | 11/2000 | Halleck et al. | |
| 6,360,615 B1 | 3/2002 | Smela | |
| 6,397,151 B1 | 5/2002 | Yamagishi et al. | |
| 6,730,047 B2 | 5/2004 | Socci et al. | |
| D494,273 S | 8/2004 | Haugland et al. | |
| 6,826,509 B2 | 11/2004 | Crisco, III et al. | |
| 6,941,952 B1 | 9/2005 | Rush, III | |
| 6,997,882 B1 * | 2/2006 | Parker .................... | A61B 5/08 600/301 |
| 7,054,784 B2 | 5/2006 | Flentov et al. | |
| 7,070,322 B1 | 7/2006 | Field et al. | |
| 7,162,392 B2 | 1/2007 | Vock | |
| 7,384,380 B2 | 6/2008 | Reinbold et al. | |
| 7,386,401 B2 | 6/2008 | Vock et al. | |
| 7,478,108 B2 | 1/2009 | Townsend et al. | |
| 7,526,389 B2 | 4/2009 | Greenwald et al. | |
| 7,693,668 B2 | 4/2010 | Vock et al. | |
| 7,747,415 B1 | 6/2010 | Churchill | |
| 7,992,421 B2 | 8/2011 | Jeftic-Stojanovski et al. | |
| 8,079,247 B2 | 12/2011 | Russell et al. | |
| 8,145,441 B2 | 3/2012 | Xi | |
| D679,207 S | 4/2013 | Johannes | |
| 8,475,371 B2 | 7/2013 | Derchak et al. | |
| 8,548,553 B2 | 10/2013 | Kamath et al. | |
| 8,548,768 B2 | 10/2013 | Greenwald et al. | |
| 8,656,072 B2 | 2/2014 | Hinkle et al. | |
| 8,766,798 B2 | 7/2014 | Howard et al. | |
| 8,926,530 B2 | 1/2015 | Stein et al. | |
| 8,961,428 B2 | 2/2015 | Spruce | |
| D727,765 S | 4/2015 | Hoshal | |
| D729,084 S | 5/2015 | Tomita et al. | |
| D731,342 S | 6/2015 | Tomita et al. | |
| 9,049,641 B2 | 6/2015 | Wible et al. | |
| 9,070,269 B2 | 6/2015 | Evans | |
| D743,822 S | 11/2015 | Borkholder et al. | |
| 9,380,961 B2 | 7/2016 | Borkholder et al. | |
| 2002/0183657 A1 | 12/2002 | Socci et al. | |
| 2005/0177335 A1 | 8/2005 | Crisco, III et al. | |
| 2006/0074338 A1 | 4/2006 | Greenwald et al. | |
| 2006/0189852 A1 | 8/2006 | Greenwald et al. | |
| 2007/0089480 A1 | 4/2007 | Beck | |
| 2009/0000377 A1 | 1/2009 | Shipps et al. | |
| 2010/0083733 A1 | 4/2010 | Russell et al. | |
| 2010/0102970 A1 | 4/2010 | Hertz | |
| 2010/0144414 A1 * | 6/2010 | Edis .................... | A63B 24/0006 463/8 |
| 2010/0251453 A1 | 10/2010 | Chen | |
| 2011/0098934 A1 | 4/2011 | Hubler et al. | |
| 2011/0105861 A1 | 5/2011 | Derchak et al. | |
| 2011/0181418 A1 | 7/2011 | Mack et al. | |
| 2011/0181419 A1 | 7/2011 | Mack et al. | |
| 2011/0181420 A1 | 7/2011 | Mack et al. | |
| 2011/0184319 A1 | 7/2011 | Mack et al. | |
| 2011/0199216 A1 | 8/2011 | Flinsenberg et al. | |
| 2011/0201972 A1 | 8/2011 | Ten et al. | |
| 2011/0203347 A1 | 8/2011 | Hower et al. | |
| 2011/0283791 A1 | 11/2011 | Jeftic-Stojanovski et al. | |
| 2011/0290018 A1 | 12/2011 | Jeftic-Stojanovski et al. | |
| 2012/0202101 A1 | 8/2012 | Ueda | |
| 2012/0280814 A1 | 11/2012 | Beale et al. | |
| 2012/0304365 A1 | 12/2012 | Howard et al. | |
| 2012/0304767 A1 | 12/2012 | Howard et al. | |
| 2013/0074248 A1 | 3/2013 | Evans et al. | |
| 2013/0110415 A1 | 5/2013 | Davis et al. | |
| 2013/0150684 A1 | 6/2013 | Cooner | |
| 2013/0226486 A1 * | 8/2013 | Henderson .......... | G01R 31/3606 702/63 |
| 2014/0276236 A1 * | 9/2014 | Swain .................. | A43B 3/0005 600/592 |
| 2015/0040665 A1 | 2/2015 | Borkholder et al. | |
| 2015/0040669 A1 | 2/2015 | Borkholder et al. | |

OTHER PUBLICATIONS

U.S. Appl. No. 14/140,613, Final Office Action dated Feb. 12, 2016, 17 pgs.
U.S. Appl. No. 14/140,613, Non Final Office Action dated Aug. 28, 2015, 20 pgs.
U.S. Appl. No. 14/140,613, Notice of Allowance dated May 6, 2016, 10 pgs.
U.S. Appl. No. 14/248,849, Advisory Action dated Mar. 17, 2016, 3 pgs.
U.S. Appl. No. 14/248,849, Decision on Pre-Appeal Brief Request dated May 5, 2015, 2 pgs.
U.S. Appl. No. 14/248,849, Examiner Interview Summary dated Feb. 25, 2016, 3 pgs.
U.S. Appl. No. 14/248,849, Examiner Interview Summary dated Aug. 27, 2015, 3 pgs.
U.S. Appl. No. 14/248,849, Final Office Action dated Dec. 18, 2014, 16 pgs.
U.S. Appl. No. 14/248,849, Final Office Action dated Dec. 18, 2015, 7 pgs.
U.S. Appl. No. 14/248,849, Non Final Office Action dated May 29, 2015, 20 pgs.
U.S. Appl. No. 14/248,849, Non Final Office Action dated Jun. 17, 2016, 19 pgs.
U.S. Appl. No. 14/248,849, Non Final Office Action dated Jul. 3, 2014, 16 pgs.
U.S. Appl. No. 14/248,849, Pre-Appeal Brief Request filed Mar. 18, 2015, 5 pgs.
U.S. Appl. No. 14/248,849, Response filed Aug. 31, 2015 to Non Final Office Action dated May 29, 2015, 11 pgs.
U.S. Appl. No. 14/248,849, Response filed Oct. 3, 2014 to Non Final Office Action dated Jul. 3, 2014, 11 pgs.
Application Serial No. 140,619, Response filed Apr. 12, 2016 to Final Office Action dated Feb. 12, 2016, 13 pgs.
U.S. Appl. No. 29/508,486, Notice of Allowance dated Jul. 21, 2015, 11 pgs.
U.S. Appl. No. 14/248,849, Response filed Feb. 18, 2016 to Final Office Action dated Dec. 18, 2015, 11 pgs.
International Application Serial No. PCT/US2014/050365, International Preliminary Report on Patentability dated Feb. 18, 2016, 10 pgs.

(56) References Cited

OTHER PUBLICATIONS

International Application Serial No. PCT/US2014/050365, International Search Report dated Nov. 24, 2014, 2 pgs.
International Application Serial No. PCT/US2014/050365, Written Opinion dated Nov. 24, 2014, 8 pgs.

* cited by examiner

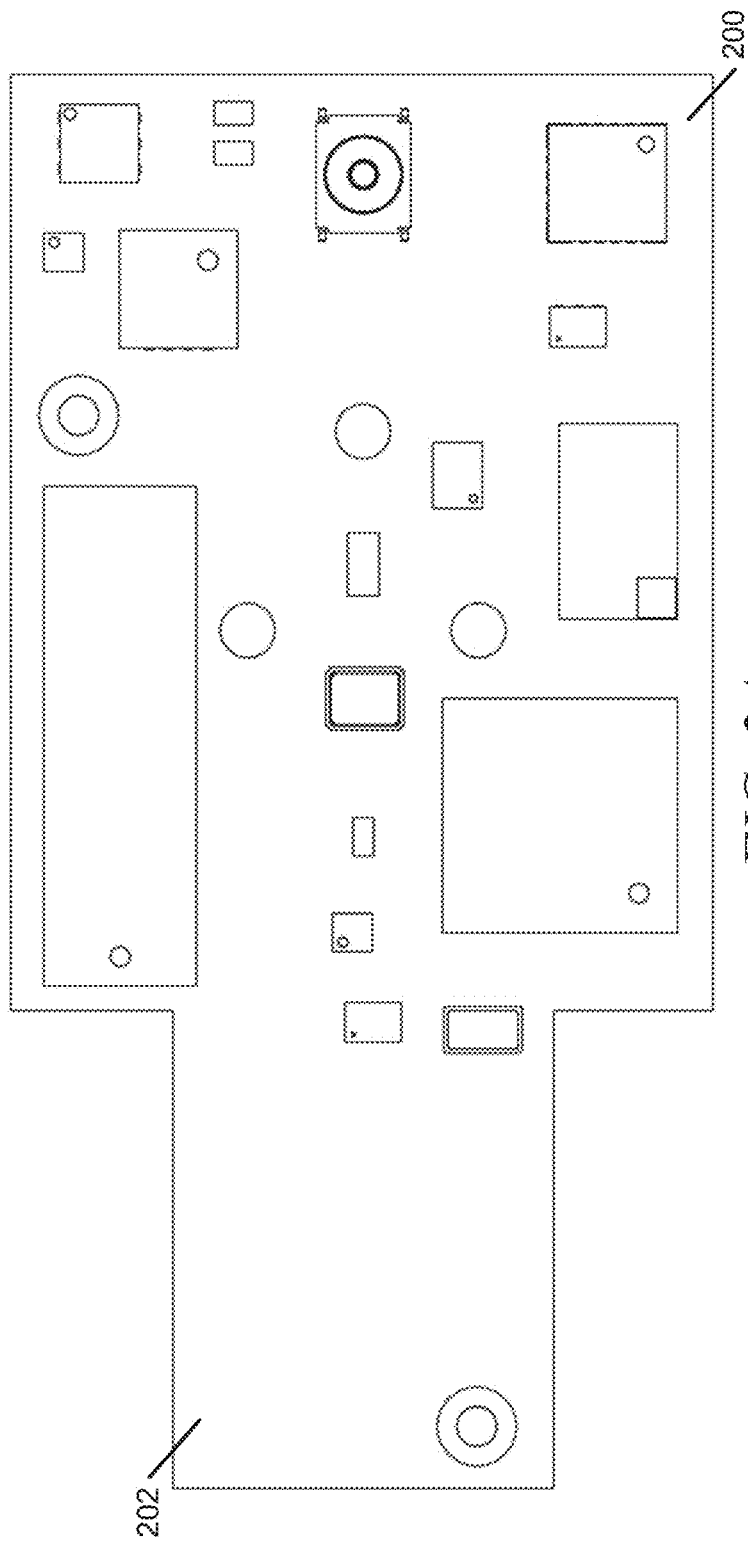
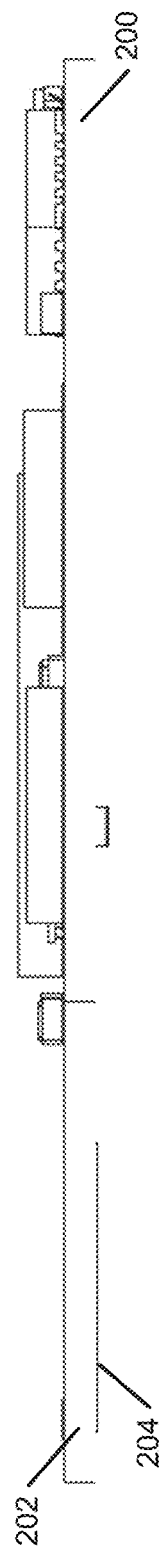
FIG. 2A
FIG. 2B

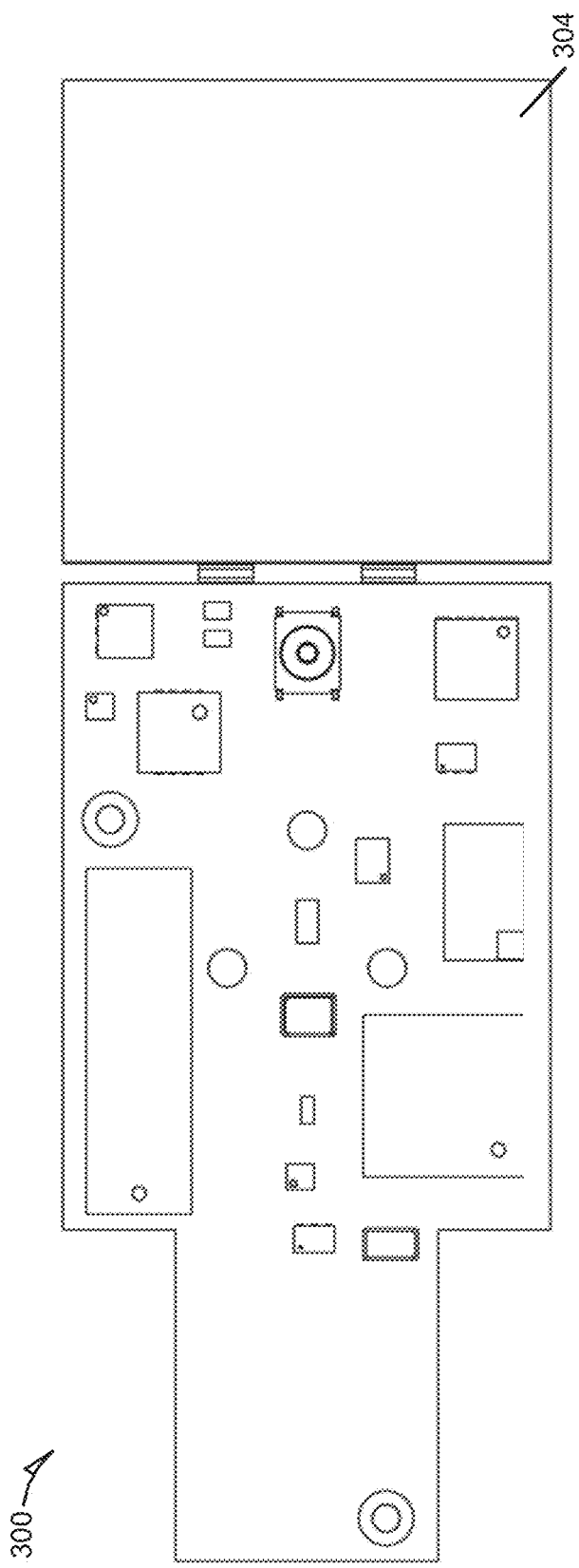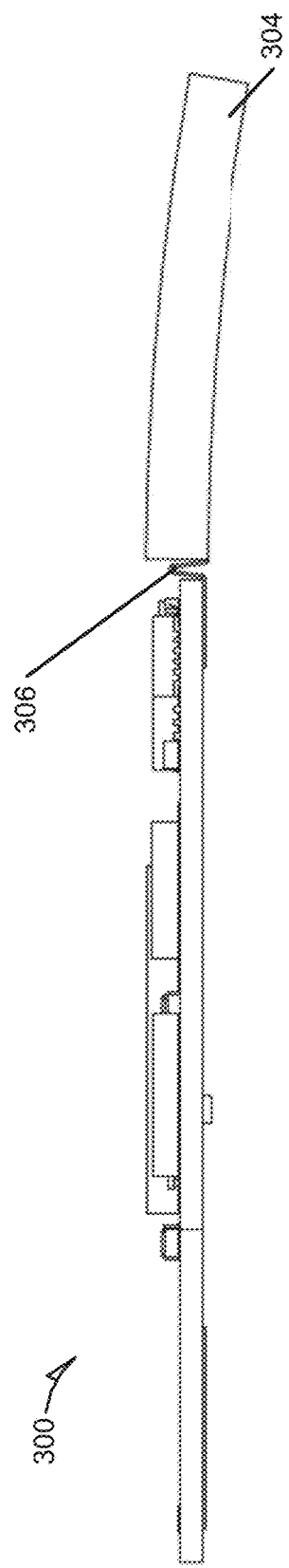
FIG. 3A
FIG. 3B

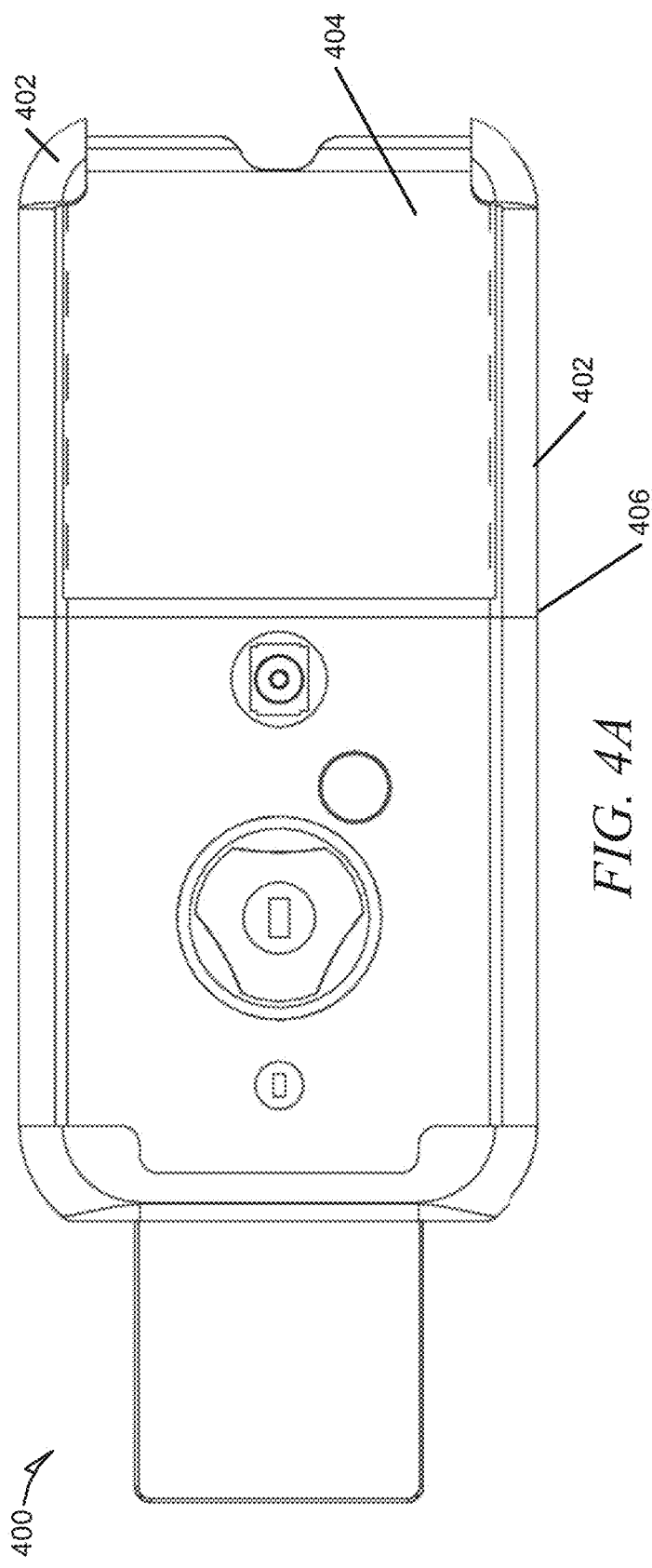
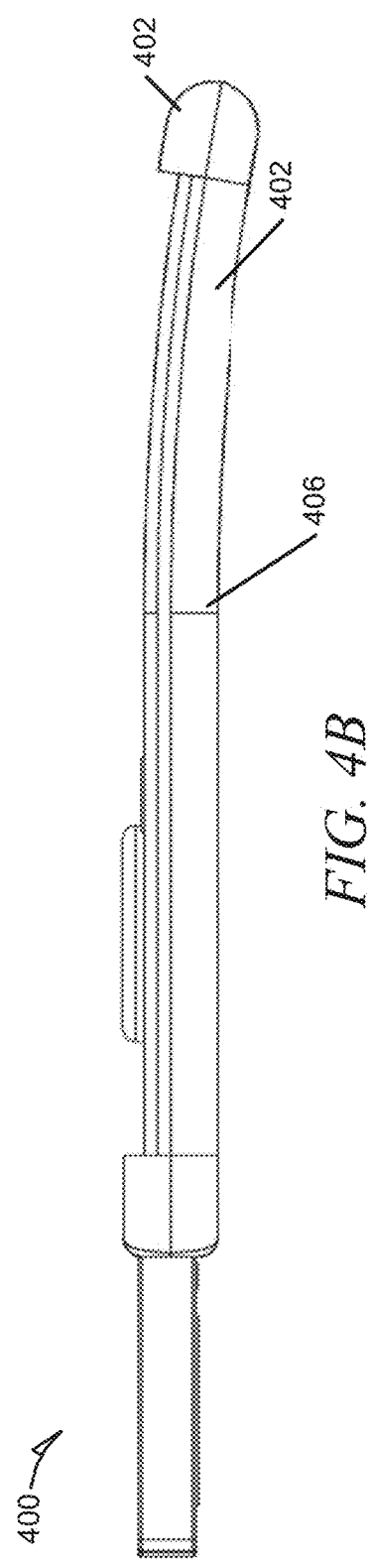
FIG. 4A
FIG. 4B

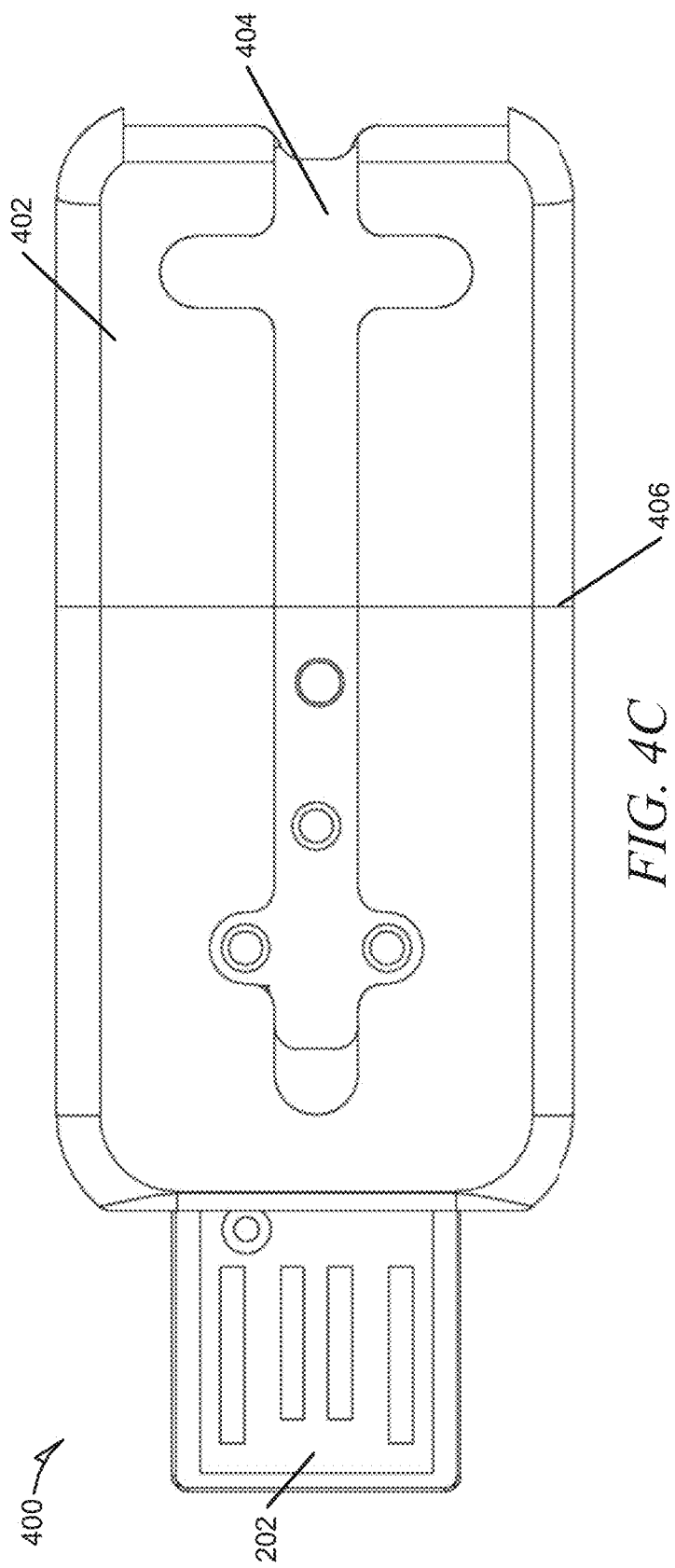
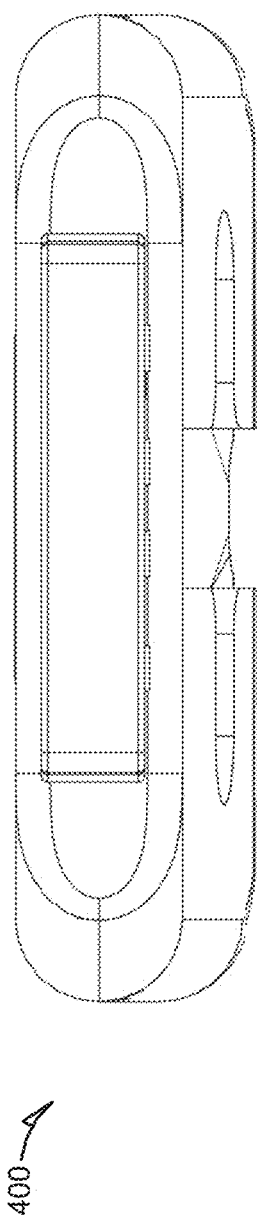
FIG. 4C
FIG. 4D

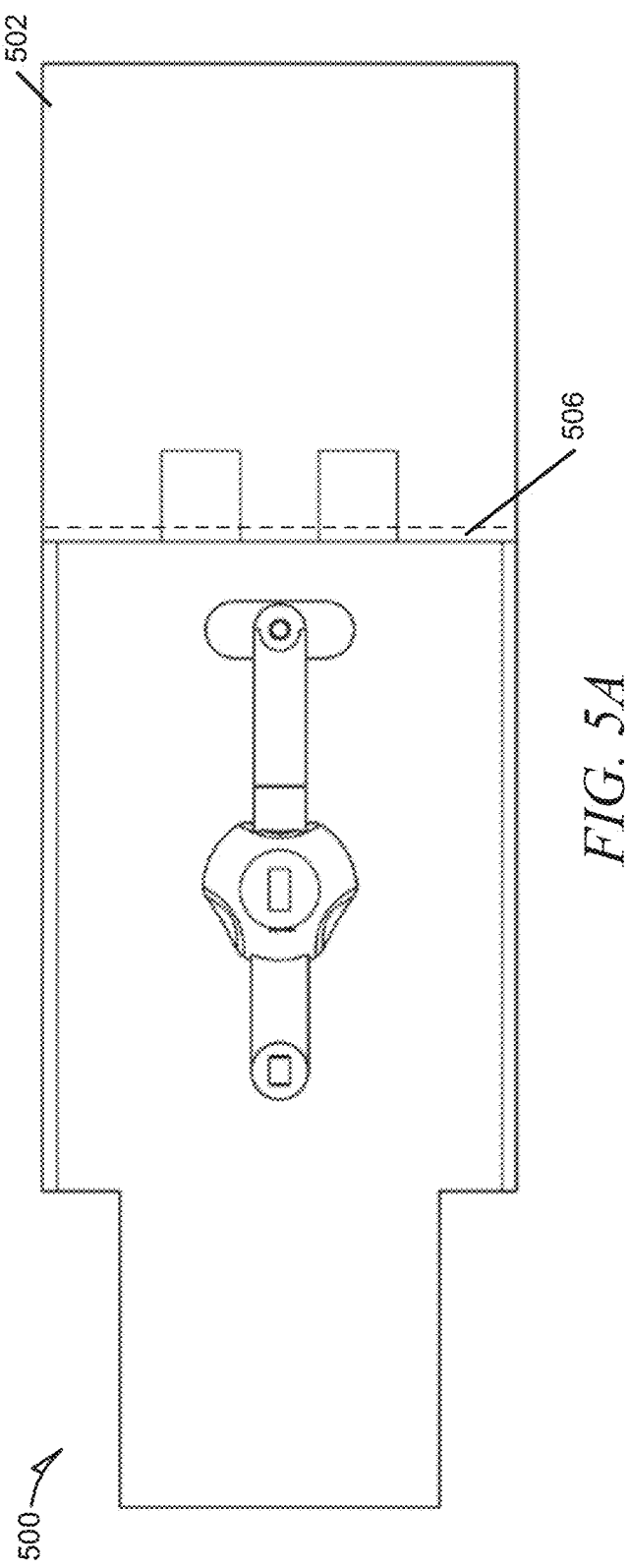
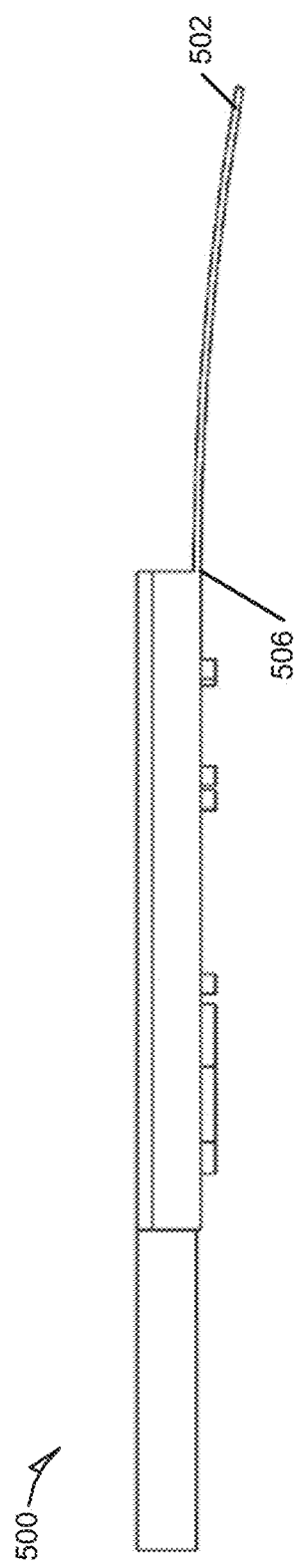
FIG. 5A
FIG. 5B

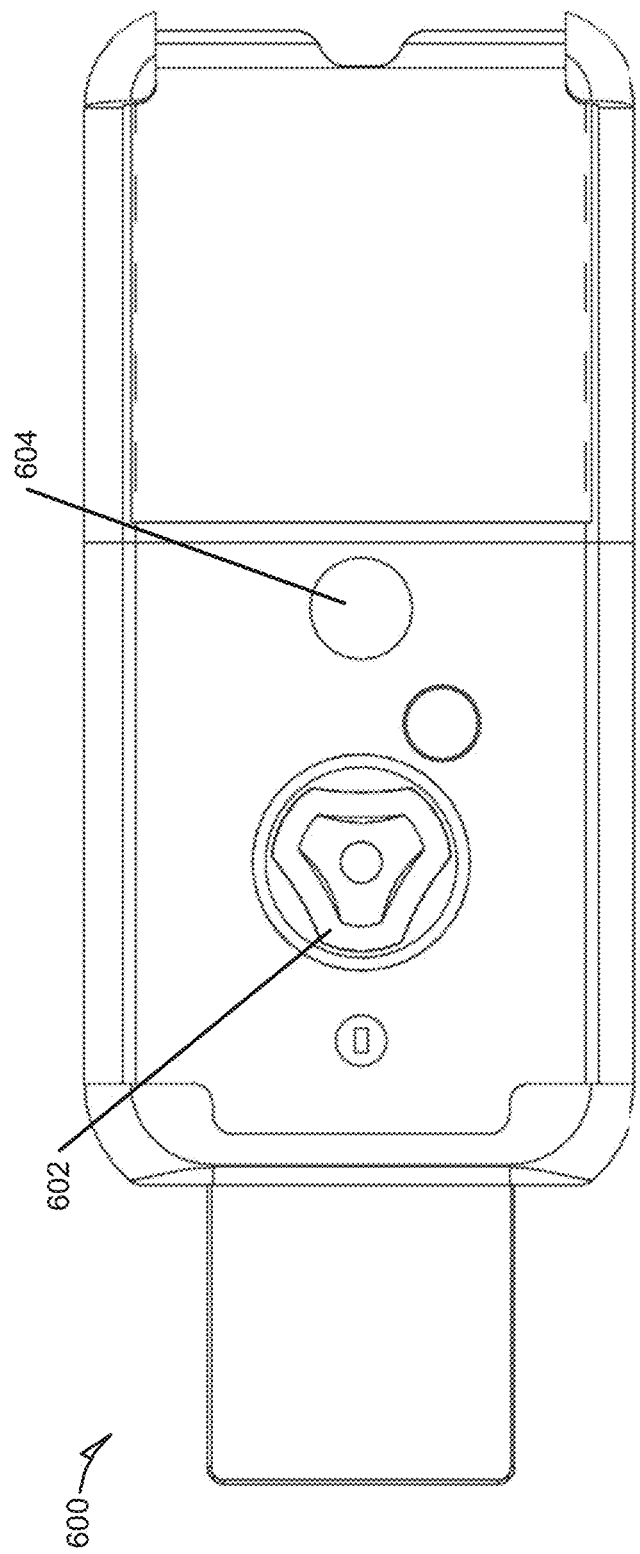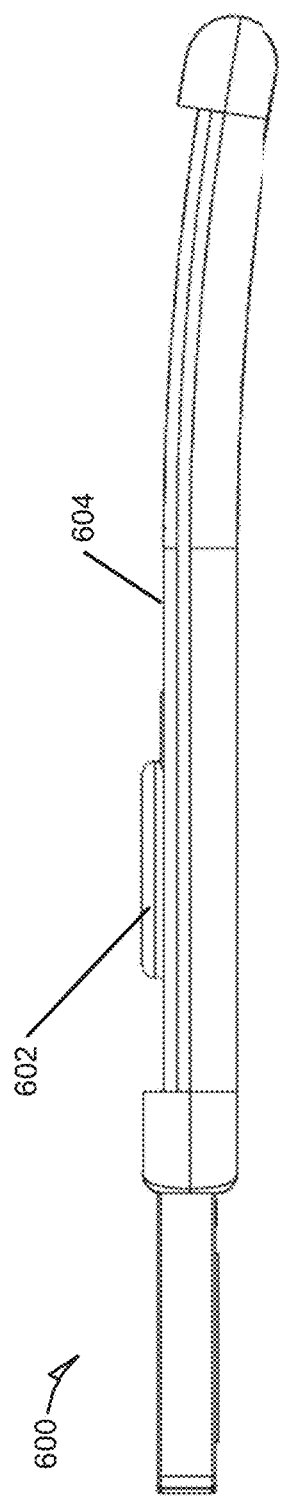

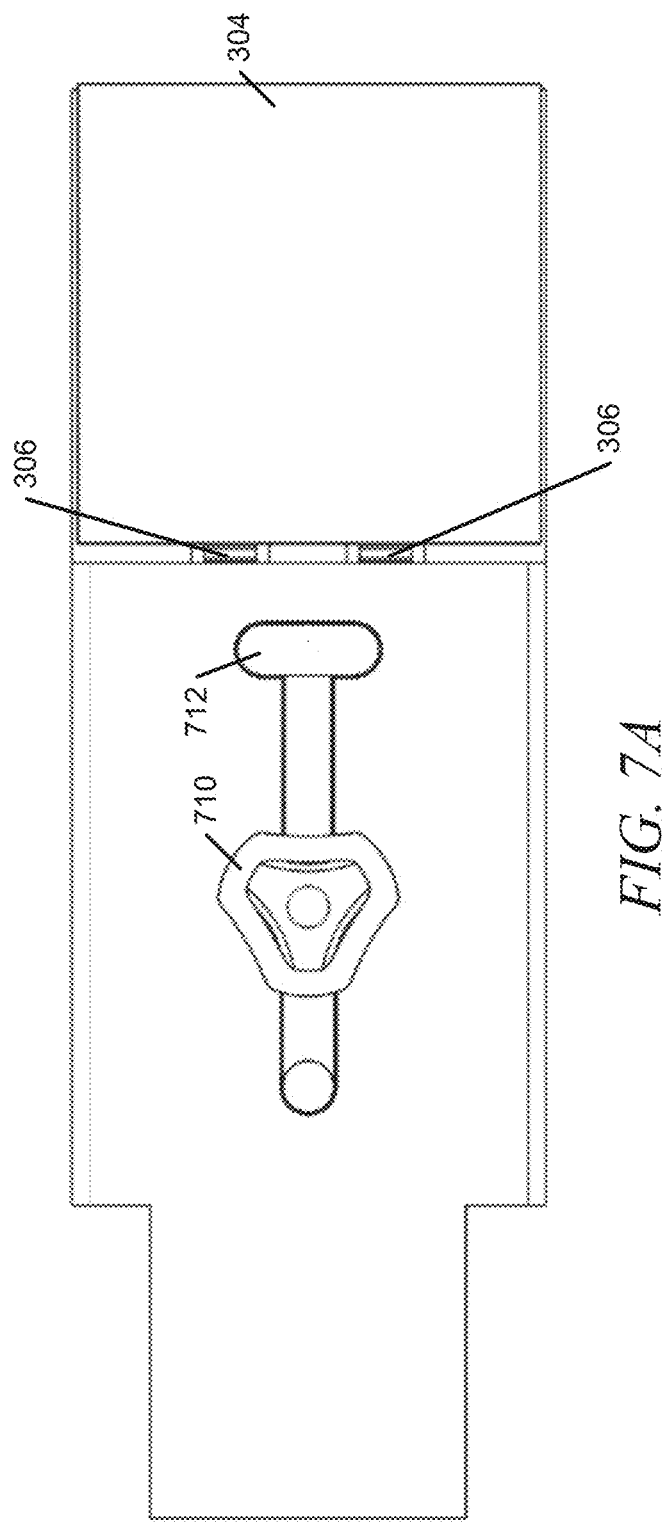
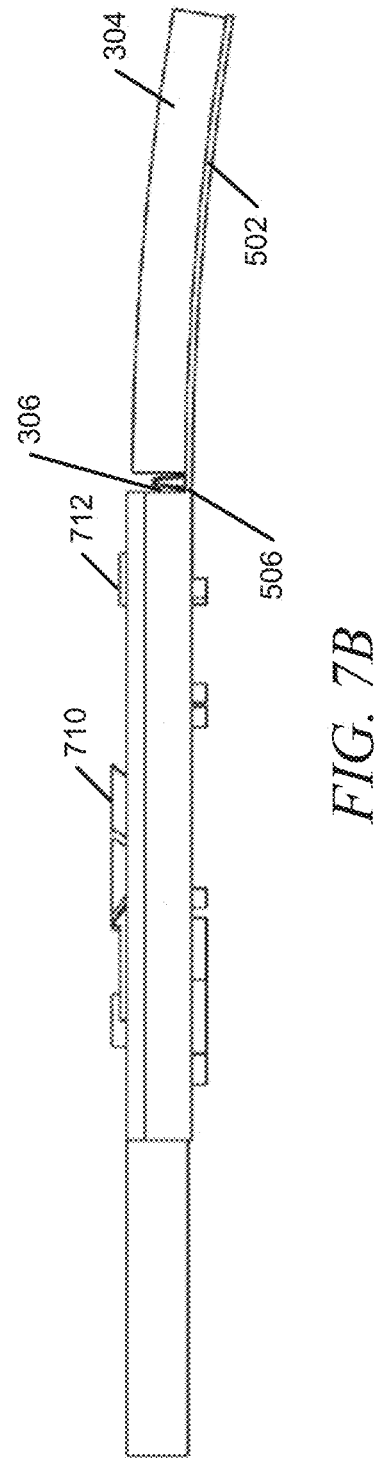
FIG. 7A
FIG. 7B

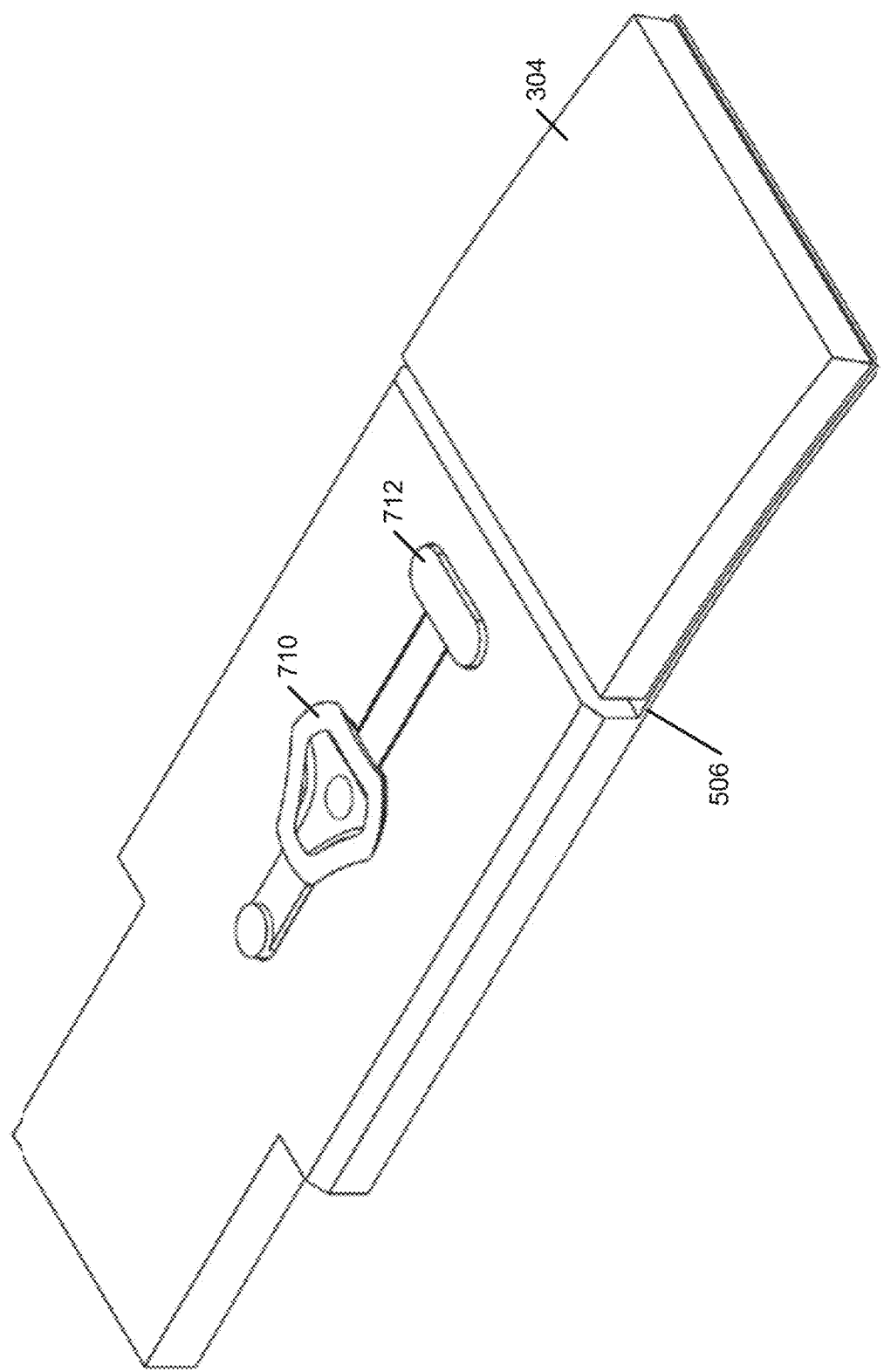

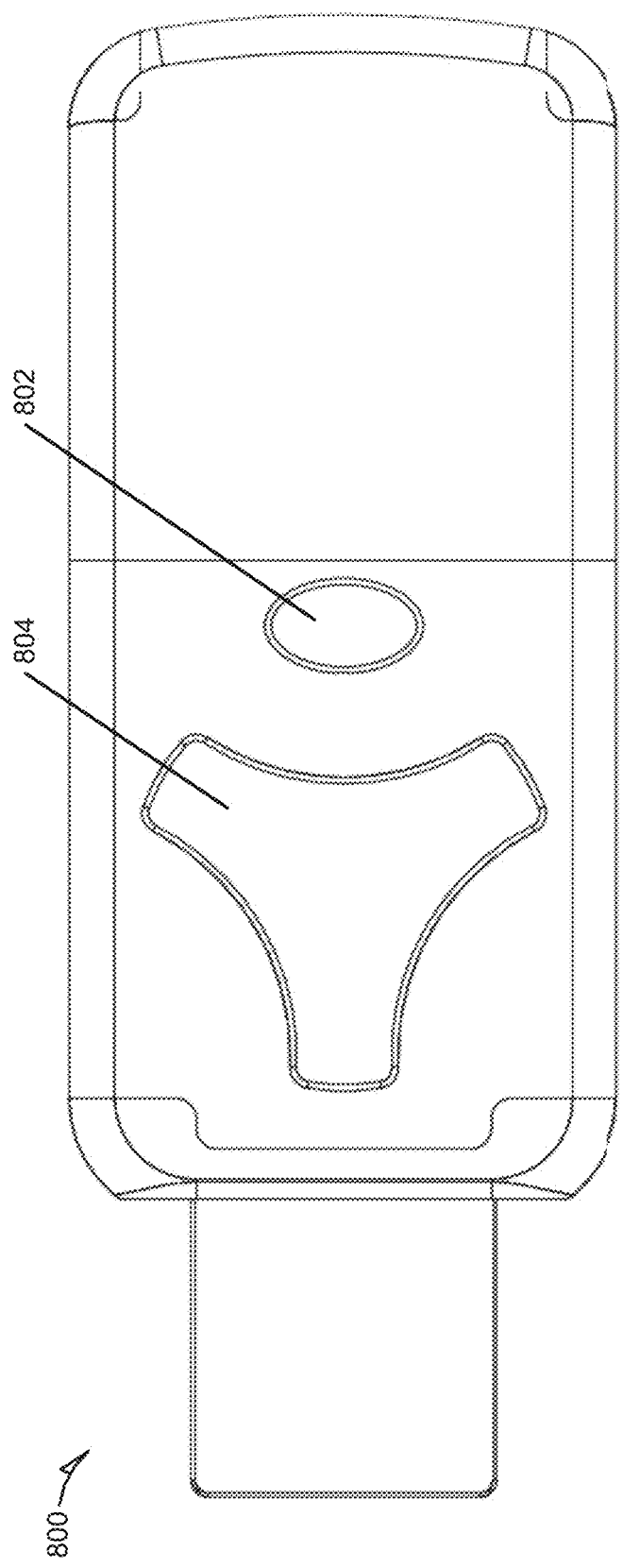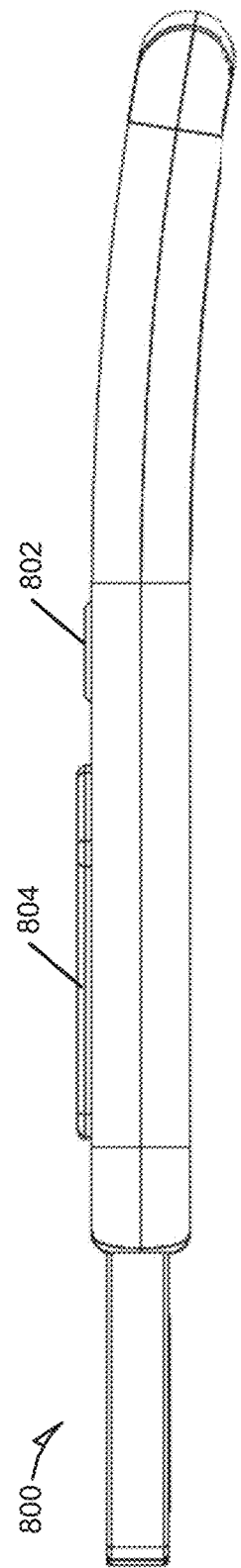
FIG. 8A
FIG. 8B

DEVICE PACKAGING FOR AN IMPACT DETECTION DEVICE

RELATED APPLICATIONS

This application is a continuation of and claims the benefit of priority under 35 U.S.C. § 120 to U.S. patent application Ser. No. 14/248,849, filed on Apr. 9, 2014, and titled "DEVICES, SYSTEMS AND METHODS FOR DETECTING AND EVALUATING IMPACT EVENTS", which is a continuation of and claims the benefit of priority under 35 U.S.C. § 120 to U.S. patent application Ser. No. 14/140,613, filed on Dec. 26, 2013, and titled "DEVICES, SYSTEMS AND METHODS FOR DETECTING AND EVALUATING IMPACT EVENTS", which claims the benefit of priority of U.S. Provisional Application No. 61/863,555, filed Aug. 8, 2013, and titled "DEVICES, SYSTEMS AND METHODS FOR DETECTING AND EVALUATING IMPACT EVENTS," each of which applications are incorporated herein by reference in their entireties.

TECHNICAL FIELD

This application relates generally to collecting and processing (e.g., analyzing) environmental sensor data, and more specifically to devices, systems, and methods for detecting and evaluating impact events.

BACKGROUND

Recent studies have indicated that undiagnosed or untreated impact injuries sustained during participation in a sport or other physical activity can have long lasting negative health implications. For example, the long term negative impact of head impacts in contact sports such as football or boxing have been well documented in the past couple decades. However, inexpensive, user friendly devices to assist in detecting and evaluating impacts sustained during sporting events and physical activity are still not widely available or commonly used.

BRIEF DESCRIPTION OF THE DRAWINGS

Some embodiments are illustrated by way of example and not limitation in the figures of the accompanying drawings in which:

FIGS. 2A-E are diagrams of an example printed circuit board assembly for a sensor device to detect impact events.

FIGS. 3A-3E are diagrams of an example printed circuit board assembly with a pre-bent battery attached prior to pre-mold.

FIGS. 4A-E are diagrams of an example pre-molded printed circuit board and battery assembly with the battery and surrounding pre-mold material forming a flexible cantilever section.

FIGS. 5A-5E are diagrams of an example pre-molded printed circuit board with a cantilever section formed during pre-mold and ready to receive a battery.

FIGS. 6A-6C are diagrams of a pre-molded impact detection device with an example light pipe and molded activation button.

FIGS. 7A-7E are diagrams of a pre-molded impact detection device with an example light pipe and activation button in position for final over-molding.

FIGS. 8A-8E are diagrams of an example over-molded impact detection device with molded activation button and light pipe.

DEFINITIONS

Figure 1:
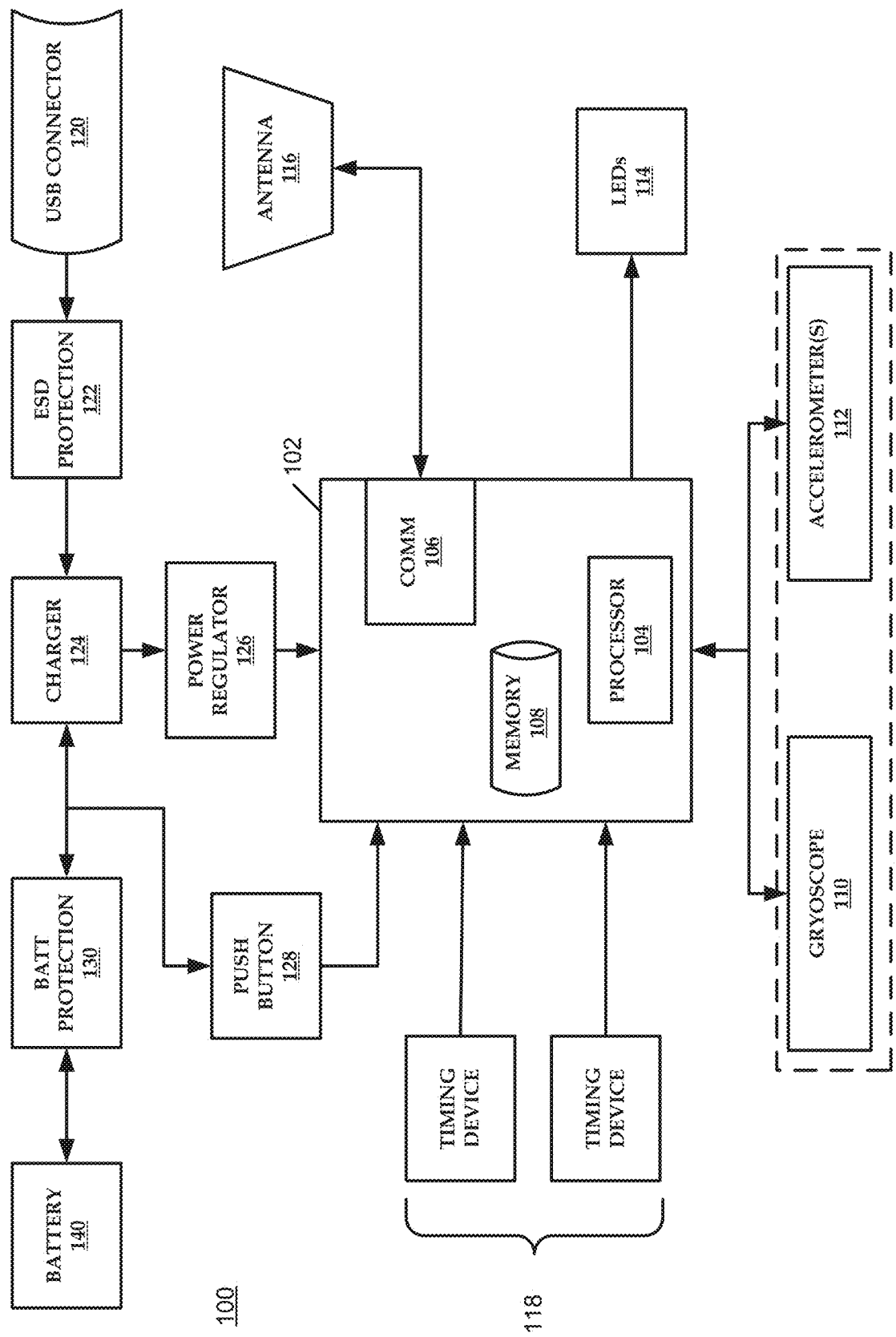
FIG. 1 is a block diagram depicting a sensor device (also referred to as an impact detection device) that can be used to detect and evaluate impact events experienced during physical activity.

Real-time—For the purposes of this specification and the associated claims, the term "real-time" is used to refer to calculations or operations performed on-the-fly as events occur or as input is received by the operable system. However, the use of the term "real-time" is not intended to preclude operations that cause some latency between input and response, so long as the latency is an unintended consequence induced by performance characteristics of the machines (e.g., computers) involved in the operation.

Overview

The following describes various examples of electronic devices including various sensors, such as high-g accelerometers and gyroscopes, to detect, record, and communicate in real-time a sub-concussive event, concussive event, or series of events that could result in a form of traumatic brain injury (TBI) to an athlete or active user. In an example, an impact detection device can detect sub-concussive events, as a plurality of such events can lead to concerns especially in the event of a subsequent more significant impact. Immediate and more reliable decision-making is made possible by providing access to impact data to assess the likelihood of concussion or other relevant injuries. The technology discussed herein identifies potential traumatic occurrences to the brain and communicates intuitive and immediate signals in real-time to smart phones, tablets, and/or computers. The user can also receive feedback directly from the impact detection device, which includes indicators and records quantitative data related to impact events. In an example, the impact detection device can provide indicators for the most recent and/or cumulative events and record quantitative data related to all events. In cooperation with existing baseline testing protocols, the technology can enhance the user's ability to detect and effectively triage concussive events. The individual impact detection devices can be personalized to account for prior events, be mounted in various ways on or in helmets, goggles, head straps, headbands, skullcaps, protective pads, and uniforms. In certain examples, the impact detection device can also measure performance attributes, such as speed, jumping height, distance traveled, steps taken, and calories burned, among others.

DETAILED DESCRIPTION

Example systems, devices, and methods for detecting and evaluating impact events are described. The devices, systems, and methods for detecting and evaluating impact events in some example embodiments may provide numerical and visual analysis of an impact event sustained by a user wearing the device. In some examples, a user can wear a sensor device during physical activities to monitor for and evaluate impact events, such as head impacts or impacts to the torso which translate to the head. In certain examples, the sensor device (impact detection device) can include algorithms, which use various internal sensors to automatically determine the position and orientation of the device. In the following description, for purposes of explanation, numerous specific details are set forth in order to provide a thorough understanding of example embodiments. It will be evident, however, to one skilled in the art that the present invention may be practiced without these specific details. It will also be evident that detecting and evaluating impact events is not limited to the examples provided and may include other scenarios not specifically discussed.

Given the increased awareness of sports-related brain injuries, an objective of a sports-focused impact detection and evaluation device and related system is to provide a platform that will assist in determining whether or not an athlete has sustained an impact that may result in an injury to the brain. The primary component of the system is an impact detection device that is worn on the head of the athlete and constantly gathers information regarding the movement of the player's head. The impact detection device can also be worn on other parts of an athlete's body and provide data that can be correlated to head impacts as well as other performance or impact type data. The data collected can then be broadcast to an application in a hand-held device or notebook/desktop/tablet computer that displays real-time information regarding the level of impact. In addition, this information can be offloaded to a backend application (a network-based or cloud computing system) responsible for maintaining the historical data regarding the athlete. One important aspect of such a system is ensuring the integrity of the data associated with an individual athlete. The association of the data with the corresponding athlete can be maintained regardless of the number of different impact detection devices the individual wears or how many different individuals are monitoring the impact detection devices.

Collecting and maintaining historical activities, movement, and impact data for individual users can assist in evaluating the health implications of subsequent events. Evaluation of historical data can assist in determining whether a player should be removed from play due to a particular event.

Impact detection devices can be worn on the head and can be attached with a headband, skullcap or be retained in a relevant position by other methods. As detailed below, the impact detection devices can incorporate accelerometers and gyroscopes to measure linear and rotational acceleration. In an example, multiple accelerometers can be used without a gyroscope to measure linear and rotational acceleration. In certain examples, the impact detection device can also incorporate a magnetometer (directional information from a magnetometer (compass) can be used to enhance certain calculations or assist in determining placement and orientation of the impact detection device on a user).

LEDs are used to indicate severity of hit based upon pre-defined algorithms and thresholds and/or user-settable thresholds. Thresholds can be selected by a user, via a web interface for example, with guidance given based upon height, weight, age, gender, sport played, and previous history of concussions of the user. In certain example, activity specific profiles can be maintained and used as a guide in assessing impact events for individual users.

An example impact detection device can store data locally and can transmit the data via wireless communication (e.g., Bluetooth Low Energy (BLE)) to a nearby mobile device. In an example using BLE, summary data can be transmitted using a broadcast advertisement, which can extend the range of wireless communications. Full-data download can be achieved with a wireless connection (e.g., BLE-paired connection) or a wired connection (e.g., Universal Serial Bus (USB) connection), among other options. Setup, configuration, and updates can be handled over a wireless connection or a wired connection.

Figure 10A:
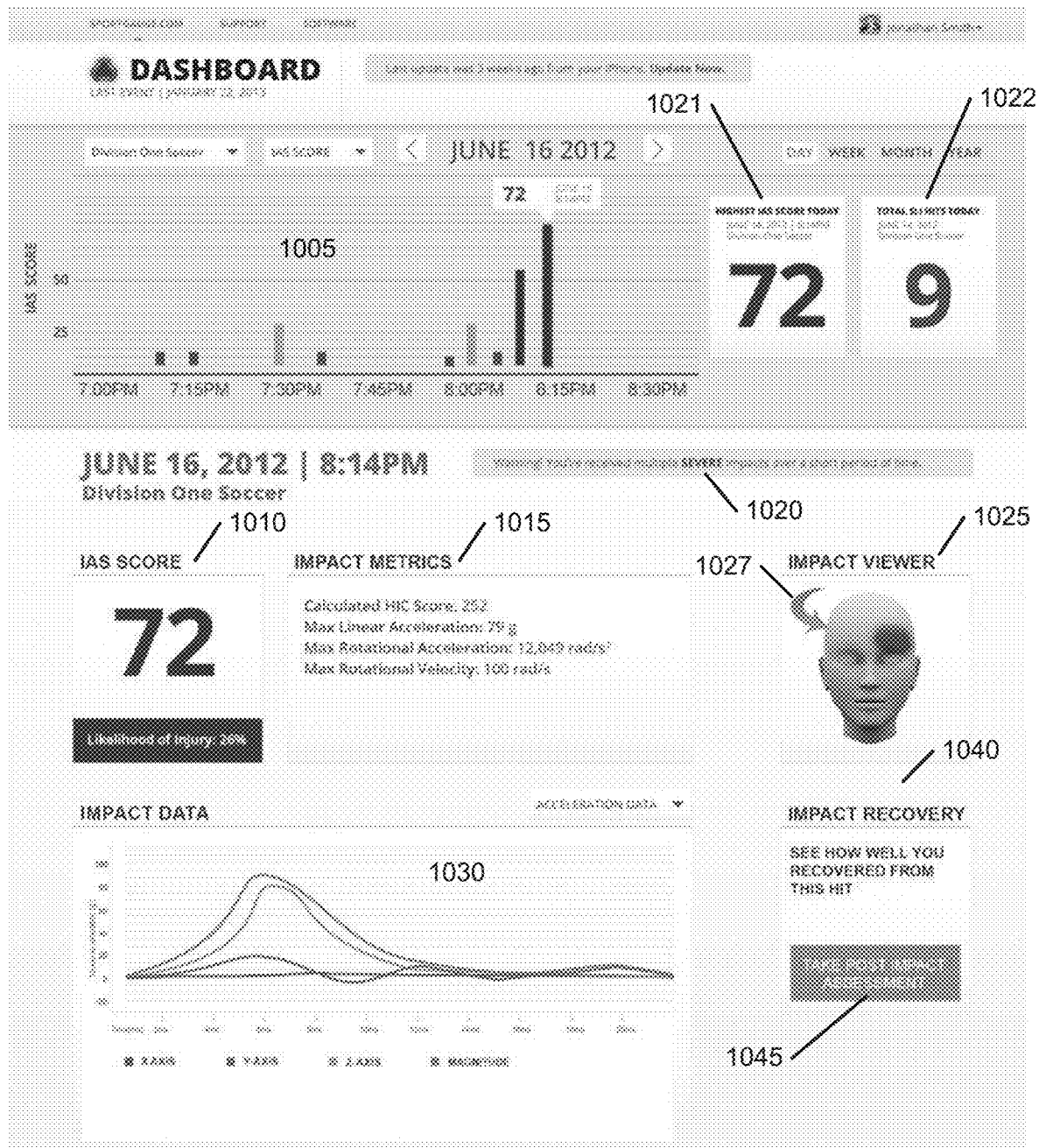
FIG. 10A is an illustration of an example web-based dashboard interface for monitoring users of an impact detection device.
Figure 10B:
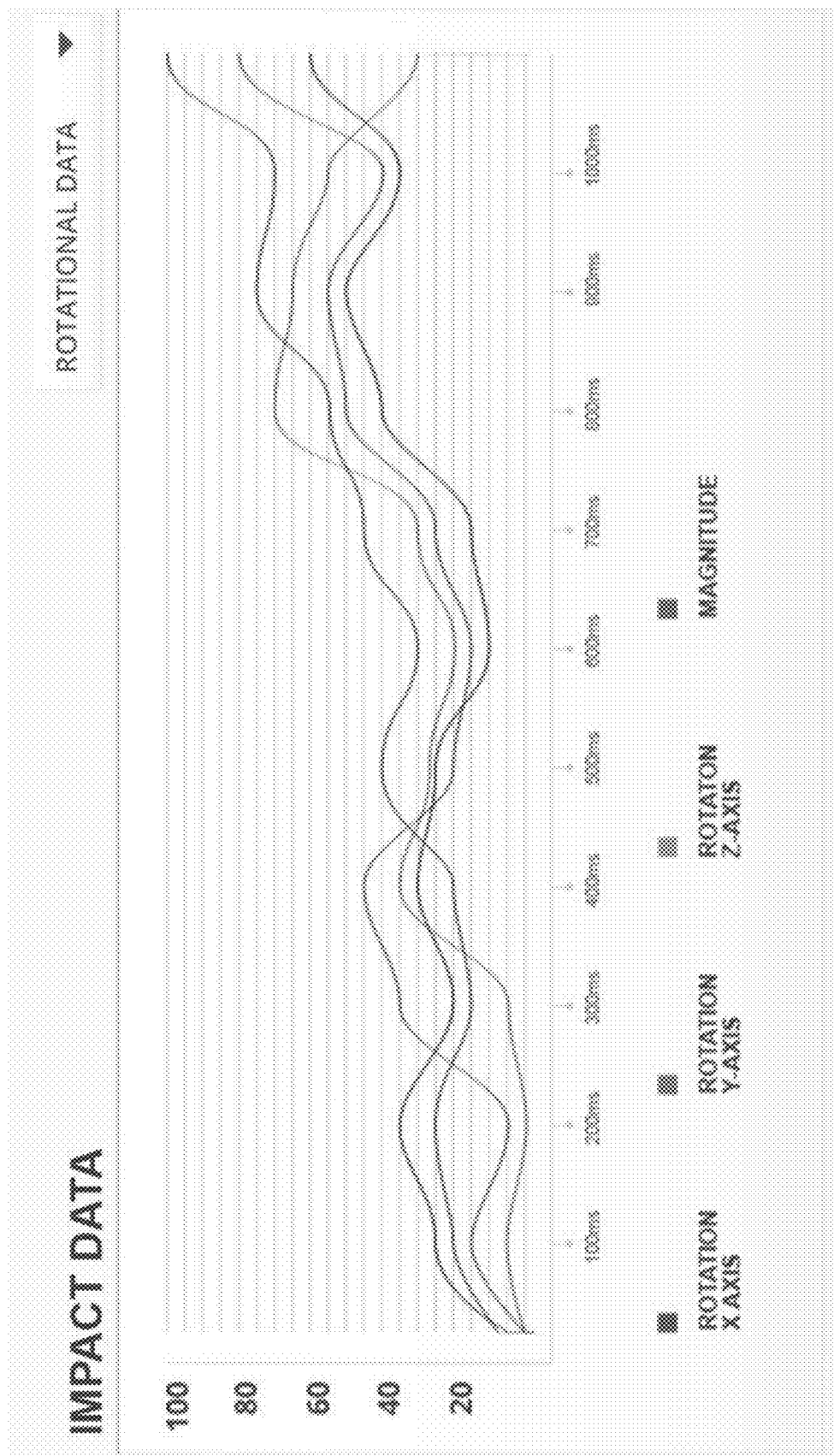
FIG. 10B is an enlarged illustration of an example Hit data graph portion of the interface illustrated in FIG. 10A.

Data collected by an impact detection device can be sent to a network-based system (also referred to as a cloud computing system), which can enable distribution to other registered mobile devices that present proper login credentials. Data can be displayed on the mobile device, native PC applications, and/or a web interface; example interfaces are illustrated in FIGS. 10A, 10B, and 11. Data can be stored in a database and can be used for future analysis and/or algorithm development. Data can be encrypted before being transmitted wirelessly or to a network-based system. The systems and devices can provide additional event or historical data to medical personal and coaches to facilitate treatment or measures to prevent further injuries.

The systems and methods, through web or mobile applications, can provide both baseline and post-event testing to detect concussion symptoms. In an example, the web and/or mobile application can implement the Sport Concussion Assessment Tool (SCAT, SCAT2 or SCAT3) and/or other base-lining tool(s). In March 2013, SCAT2 was superseded by the SCAT3, which provides an assessment for athletes 13 years and older issued coincident with the Consensus Statement issued after the 4th International Conference on Concussion in Sport held in Zurich in November 2012, and a modified version (Child SCAT3) was issued for children aged 5 to 12 years. The SCAT, original, 2, or 3, takes about 15-20 minutes to complete and computes a composite score (composite score is comprised of the Glasgow Coma Scale, a Standardized Assessment of Concussion (SAC) score (cognitive and physical evaluation, delayed recall), and a balance assessment score (modified Balanced Error Scoring System or BESS).

In other examples, a different comprehensive baseline test can be used to provide a basis for re-testing to assess impact events and evaluate recovery. The system can also provide a quick assessment sideline test (e.g., less than 5 minutes) for quick evaluation of a player after a recorded impact event. The quick assessment sideline test can be a sub-set of a comprehensive baseline test. In an example, the system can implement 3 different levels of testing, a comprehensive baseline test, a quick sideline assessment that uses a small sub-set of questions from the comprehensive baseline test, and a post-game assessment that can include an expanded sub-set of questions but less than the comprehensive baseline test. In certain examples, real-time data from an impact detection device can be leveraged to assist in determining the level of assessment testing performed in a given scenario. For example, if the impact detection device provides an indication of a high severity impact, a more detailed assessment test may be recommended. Regardless of the assessment test used, data from the impact detection device can be integrated into the results to assist in providing a comprehensive assessment of injury risk.

In some examples, post-impact event assessments can collect and integrate additional information from an impact detection device. For example, part of a post-impact event assessment can include balance tests that can collect information directly from an impact detection device to quantitatively measure performance of a user during a balance test. Data from the accelerometers and/or gyroscope within the impact detection device can provide an objective measure of how a user's balance (or other physical capabilities) was affected by the impact event. In an example, baseline balance (or other physical capability) data can be collected during a setup procedure for future comparison purposes.

The devices, systems, and methods described herein can also be used for injury avoidance training. Feedback from impact detection devices can be used during training and practice to correlate specific techniques to head impacts, which can then be used to modify player behaviors. For example, soccer players routinely play the ball with their heads, and often practice performing such maneuvers. However, it is well known that soccer players often "head" the ball incorrectly, which can result in a significantly increased chance of injury. An impact detection device can be used during practice to assist in determining correct safe head contacts from incorrect and potentially unsafe ones. The impact detection device, data collection capabilities, analysis algorithms, and graphical displays can be modified for use in the training environment. Data recording during training drills can be collected, analyzed, and displayed within a user interface to assist coaches and players in assessing technique. In an example, data collection, analysis, and results display can occur in near real-time utilizing a mobile computing device available on the practice field. The collected data can identify techniques that result in higher than acceptable impact levels.

In some examples, a user can utilize multiple impact detection devices simultaneously and the analysis system can integrate the data to better characterize impact events. For example, a user can wear one impact detection device on their head and another on their torso, which allows an analysis system to make a differential determination of head acceleration relative to the user's body. Relative acceleration data can be used to refine injury risk assessments for a particular event.

Example impact detection devices are rechargeable via USB connection and can make use of activity modes for power reduction when the device is not being worn or the user is not in active play. In an example, the gyroscopes or accelerometers can be polled to determine if the device is inactive, enabling power to be reduced or the device to automatically shut down. The integrated USB connection allows for easy and convenient recharging options. Most modern automobiles include a USB connection that can be used for last minute recharging on the way to an event. Similarly, the commonality of USB recharging options extends to cell phone recharging devices or just about any mobile computing device. An additional advantage of the integrated USB is that no additional cable or accessory is required for recharging for wired data download to common computing platforms, such as a laptop computer.

The devices, systems, and methods can include the following algorithms, some of which are described in greater detail in reference to specific figures below:
  Impact location
  Impact detection
  Sensor location
  False positive rejection
  Data reduction
  Risk injury assessment
  Translation of coordinates to center of head
  Classification of activity levels and/or movement types The devices, systems, and methods can also provide athletic performance metrics including, but not limited to:
  Step count
  Speed (max, min, average)
  Calories burned
  Max air time
  Highest vertical jump
  Agility metric
  Distance traveled Example Sensor Devices FIGS. 1 through 8E illustrate different aspects of an example impact detection device in various stages of manufacture. The figures are intended to illustrate certain aspects both mechanical and electrical that play a role in enabling detection and evaluation of impact events during various physical activities.

An objective of the impact detection devices discussed herein is to allow for flexibility and conformance to a wide variety of head shapes and sizes, while having a mechanical structure that protects the electronic components from mechanical forces, physical impacts, sweat, weather, dirt, debris, dust, and other environmental contaminants. The packaging discussed below also creates a comforting feel, enables charging and data transfer, and attains a quality look and feel, among other things. Data transfer and charging can be enabled via an integrated Universal Serial Bus (USB) connector, which utilizes a widely used standard for connectivity for electronic devices.

In an example, the illustrated device will be worn on the head and can conform to the majority of head shapes and sizes when gently compressed by a mounting mechanism (e.g., head band or skull cap, among other head coverings or athletic devices). Conforming to various head shapes and sizes, while maintaining a protective structure, provides benefits that can include improved data collection, user acceptance, and device robustness, among others.

In an example, the impact detection device can incorporate a rigid Printed Circuit Board Assembly (PCBA) with an integrated male USB A connector. The rigid PCBA can be over-molded with a plastic or similar polymer coating selected to provide certain desired characteristics, such as flexibility through controlled durometer, and environmental protection through minimal moisture absorption and high adhesion (this operation is also referred to as the pre-mold operation to distinguish it from a second over-molding operation that can be performed on the complete impact detection device). In certain examples, the pre-mold includes a cantilevered section, which can hold a battery and allows for flexing and bending of at least a portion of the overall device. In certain examples, instead of merely creating the cantilever section, the pre-mold operation can capture the battery on/within the cantilever section and still maintain flexibility at the joint between the PCBA and battery. In certain examples, both the cantilevered section and the battery form a moldable section that can conform to a certain radius and flexes in relationship to the PCBA portion of the impact detection device. In an example, PCBA, cantilever section, and battery are initially formed with the cantilever section and battery curved at approximately a 110 mm radius. Other initial radii can be used depending upon the intended wearing location or target anatomical structure. For example, the PCBA, cantilever section and battery assembly can be formed into a tighter radius during manufacture or during use by an end user. In this example, the amount of flex in the cantilever section between the PCBA and the battery can be approximately negative 20 degrees and positive 10 degrees, with an initial angle of approximately negative 9 degrees (an example negative initial angle is illustrated in FIGS. 3B, 4B, 5B, 6B, 7B, and 8B).

In certain examples, adhering a flexible metal, or similar material, under both the PCBA and the battery, can create a cantilevered section. In yet other examples, the battery can include a flexible cantilevered section that can be adhered under the PCBA to provide flexibility between the PCBA and the battery portion. In all of these examples, a pre-mold operation can be utilized to capture the various portions of the assemblies.

In an example, the pre-mold can include locating features to enable placement of a light pipe and button actuator assembly. The light pipe and button actuator assembly (an example of which is illustrated in FIGS. 6A-7E) can be held in place with ultra-violet, thermal, or time-based curing optical grade epoxy, or other suitable adhesive. Alternately, features in the pre-mold can couple with features in the light pipe to mechanically lock the assembly in place. In other examples, no button actuator assembly is used; rather a piece of flexible material is aligned with the underlying button and over-molded to form an integrated button.

In an example, the battery can be pre-bent into a desired shape and at least partially encapsulated by the pre-mold process. In this example, the cantilever section surrounds at least a portion of the battery (e.g., FIGS. 4A-4E). In certain examples, the battery can be bent into a permanent shape during or prior to adhering it to the cantilevered section formed during the pre-mold operation, the permanent shape is selected to match the curvature of the head. In another example, the cantilevered section formed during the pre-mold operation is sufficiently thin to allow for bending of the battery section relative to the PCBA section after the device has been over-molded for final packaging. In an example, the cantilever section of pre-mold material can be between 2 mm and 7 mm thick, with a preferable thickness as thin as manufacturing techniques and mechanical robustness will allow. In yet other examples, the cantilevered section and the battery can be a deformable metal that allows an end user to permanently or semi-permanently deform the shape of the impact detection device to a desired configuration suitable for the wearing location. In still other examples, the cantilever section can be formed around the battery with the entire section maintaining a level of flexibility or bendability. In some examples, materials with different durometer measurements can be selected to obtain the desired level of flexibility versus rigidity. For example, a material with a lower durometer measurement may be selected for the pre-mold material to favor flexibility over rigidity. In an example using a higher durometer material, the flexibility characteristics of the flex zone will primarily determine the overall flexibility of the impact detection device. In a certain example, the pre-mold material used can have a durometer measurement between Shore 75A and Shore 73D. The different methods and stages of manufacture of example impact detection devices are illustrated in reference to FIGS. 3A-8E, which are discussed below in a section titled Example Mechanical Structure.

Once the pre-mold and ancillary component assembly is complete, the example impact detection device can receive a final over-mold with a soft rubbery or similarly malleable material to provide the desired aesthetics, feel, and environmental protection, at least in this example. In other examples, the over-mold material can be harder and less flexible. The male USB A connector may not receive any additional over-molding during this process, leaving only the connector and the harder pre-mold exposed on one end. The final over-mold also allows for flexing/bending between the PCBA and the cantilevered battery area, making the impact detection device at least segmentally flexible that allows for conformance to a variety of wearing locations, shapes, and sizes.

FIG. 1 is a block diagram depicting a sensor device 100 (also referred to herein as an impact detection device) that can be used to detect and evaluate impact events experienced during physical activity. The sensor device 100 can include a processing and communication module 102, a gyroscope 110, an accelerometer 112, LEDs 114, an antenna 116, one or more timing devices 118, a USB connector 120, optional ESD protection circuitry 122, a charger 124, a power regulator 126, a push button 128, optional battery protection circuitry 130, and a battery 140.

The processing and communication module 102 can include a communication module (Bluetooth and/or other wireless) 106, a memory device 108, and a processor 104. The communication module 106 can be used to operatively couple and communicate between the sensor device 100 and one or more external computing or storage devices, although other types and numbers of communication networks or systems with other types and numbers of connections and configurations can be used. The processing and communication module 102 includes one or more processors 104 internally coupled to the memory 108 by a bus or other links, although other numbers and types of systems, devices, components, and elements in other configurations and locations can be used. The one or more processors (e.g., processor 104) in the sensor device 100 can execute a program of stored instructions for one or more aspects of the present technology as described and illustrated by way of the examples herein, although other types and numbers of processing devices and logic could be used and the processor could execute other numbers and types of programmed instructions. The memory 108 in the sensor device 100 can store these programmed instructions for one or more aspects of the present technology as described and illustrated herein, although some or all of the programmed instructions could be stored and executed elsewhere. A variety of different types of memory storage devices, such as a solid-state memory, can be used for the memory 108 in the sensor device 100. The memory 108 can be either internal to the microprocessor, an external integrated circuit or a tangible storage media device. In an example, the memory 108 can also be used to store impact event data as well as other metrics.

Although an example of the sensor device 100 is described herein, it can be implemented on any suitable computer system or computing device. It is to be understood that the devices and systems of the examples described herein are for exemplary purposes, as many variations of the specific hardware and software used to implement the examples are possible, as will be appreciated by those skilled in the relevant art(s).

The accelerometers 112 can include a low-g (for example ±16 g) three-axis accelerometer to capture linear acceleration in three axes, although other types, such as a high-g accelerometer (for example >=±200 g), and numbers of inertial measurement units could be used. In an example, the accelerometers 112 can include two (or more) three-axis accelerometers. Accelerometers 112 can record linear acceleration, which can be used in impact severity calculations. Linear acceleration can also be used in event detection, device position and orientation calculations, power-saving mode detection, and button tap interface. In certain configurations, the accelerometers 112 (at least two accelerometers spatially separated) can also detect angular acceleration, which can be used in event detection, device position and orientation calculations, and power saving mode detection.

The gyroscope 110 can record angular velocity to be used in impact severity determinations. The angular velocity can also be used in other algorithms, such as event detection and device position and orientation calculations. The gyroscope 110 can be a single axis, multi-axis, or a combination of single axis gyroscopes. In certain examples, the gyroscope 110 and accelerometers 112 can be combined into a single package.

The communication module 106 can be used to interface with external components. Impact event data as well as other metrics can be transmitted to nearby wireless devices to provide real-time information to the user. A wireless interface can be implemented as BLE or other current or future developed wireless standard. In an example, use of low power wireless standards, such as BLE, can assist in reducing overall power consumption. In other examples, the communication module 106 can support one or more wireless communication technologies, such as Bluetooth low energy, Bluetooth, Zigbee, WiFi, NFC, RFID, or any other existing or future standards.

The communication module 106 can also control communication over a wired connection, such as supplied by USB connector 120. The USB connector 120 can include a connection for charging and/or communications, such as an integral USB male connector. The USB connector 120 can be integral with the PCB with contacts formed by pads on the PCB surface. The USB connector 120 can be a plastic USB male connector with embedded contacts that is over-molded to become an integral component of the impact detection devices. Alternative connectors for the USB connector 120 can include a female micro-USB connector, a headphone jack, a proprietary (non-standard) connector, or other connections with data transmission and charging capabilities.

LEDs 114 can be used as indicators for impact event severity, battery status, data transfer, charging, wireless connection, and power cycle status. LEDs 114 can use colors or other methods, such as blink rate or intensity, to indicate severity. LEDs 114 can include indicators for triage (red, yellow, green). Alternatively, LEDs 114 can include two LEDs can be used (red/green) with mixing to achieve yellow. A light pipe design for improved mixing, uniform illumination intensity, and shape definition can also be included. In certain examples, the LEDs 114 can be replaced with Bi-stable display technology for indicators of an event (e.g. E-skin) or an integral display (such as LCD or E-ink).

The antenna 116 can be used to transmit and receive signals over a wireless communication connection. The power regulator 126 can provide a regulated voltage to the system 100. The push button 128 can provide a user interface to the system 100. The USB connector 120 can enable charging and data transfer. The charger 124 can route power from an external power source to a rechargeable battery, such as battery 140. The battery protection circuit 130 can prevent battery overvoltage, under-voltage, or over-current conditions. The timing devices 118 can be crystals or similar timing devices used for maintaining real-time clock, communication timing, and other microcontroller timing functionality.

The impact detection devices can also include hardware to facilitate power harvesting, wireless power transfer, and sensors to sense when the impact detection device is placed on the head or other body part or uniform of a user (e.g. capacitive, thermal, infrared, reflectance).

The impact detection device can link to a stand-alone wireless capable device (e.g. smart phone, computer, wrist-worn device (e.g. watch for referee)). An impact detection device can link to single or multiple mobile devices, with security code control. Data delivered can be summary or full event data. Two-way communication capability to update risk assessment criteria on an impact detection device based on latest updates in algorithms is also supported by the hardware described above. Data offloaded from an impact detection device can be GPS tagged, for example by a smartphone, before upload to network-based system (e.g. cloud).

Event data generated by an impact detection device can be date and time stamped with actual date and time or date and time relative to current connection/download time, among others. Impact detection device clock can be synchronized when linked to wireless device (e.g. smart phone).

Example Mechanical Structure

The following discussion and associated figures describe a particular example mechanical structure design to provide a solution to various problems. The first problem addressed by the illustrated design involves balancing trade-offs between flexibility and robustness. A completely flexible electronic device is likely to encounter reliability and durability problems during real world use. In contrast, a completely rigid device can diminish comfort, fit, accuracy, and use of this type of device. The following describes a segmentally flexible device that provides sufficient flexibility to provide user comfort and good fit (promoting improved measurement accuracy) while maintaining rigid robust packaging for critical components.

Printed Circuit Board Assembly (PCBA)

Figure 2C:
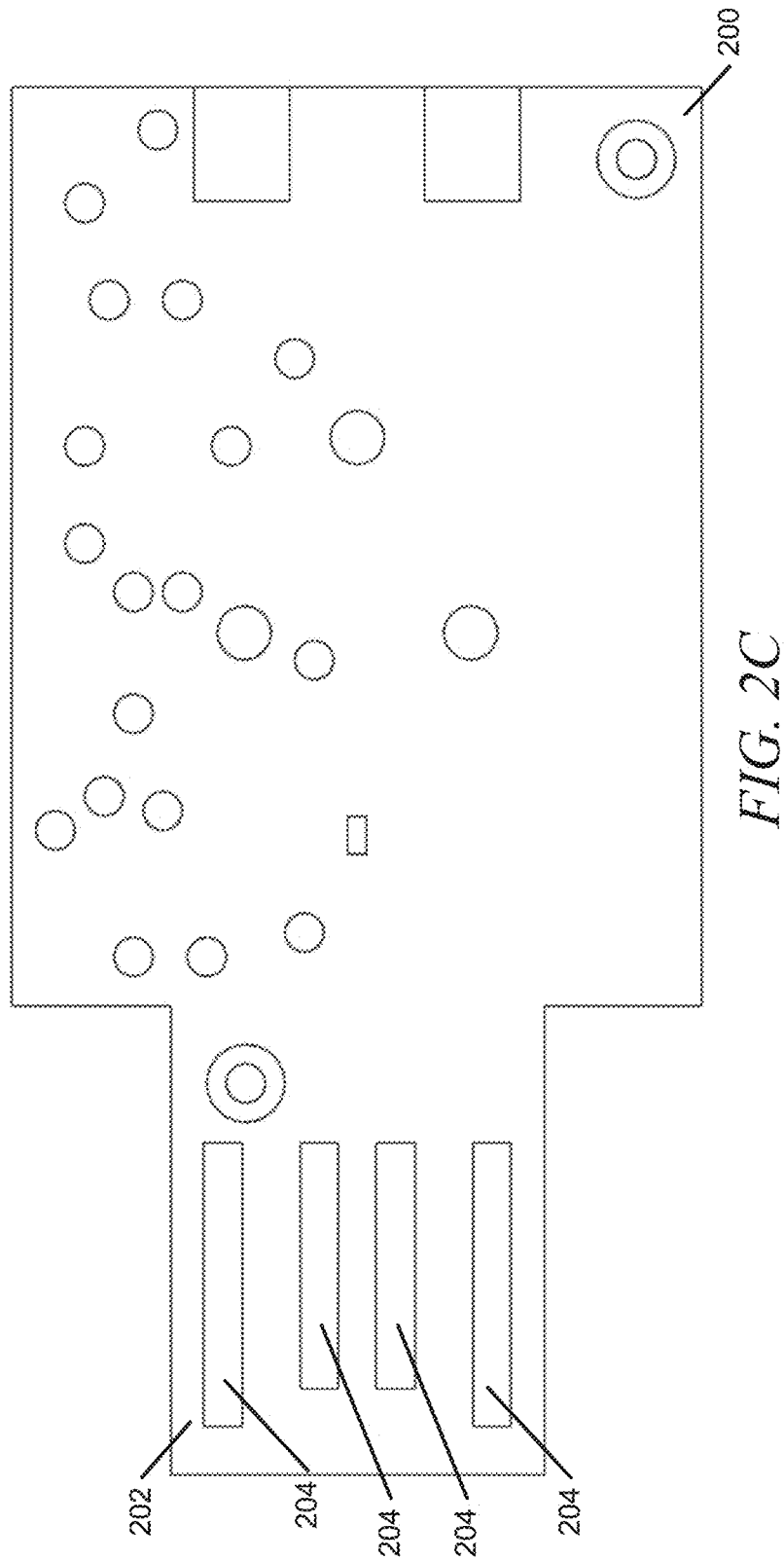
Figure 2D:
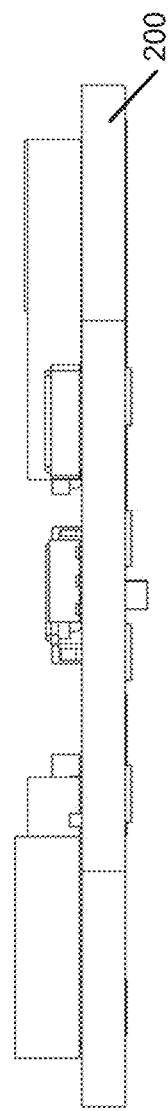
Figure 2E:
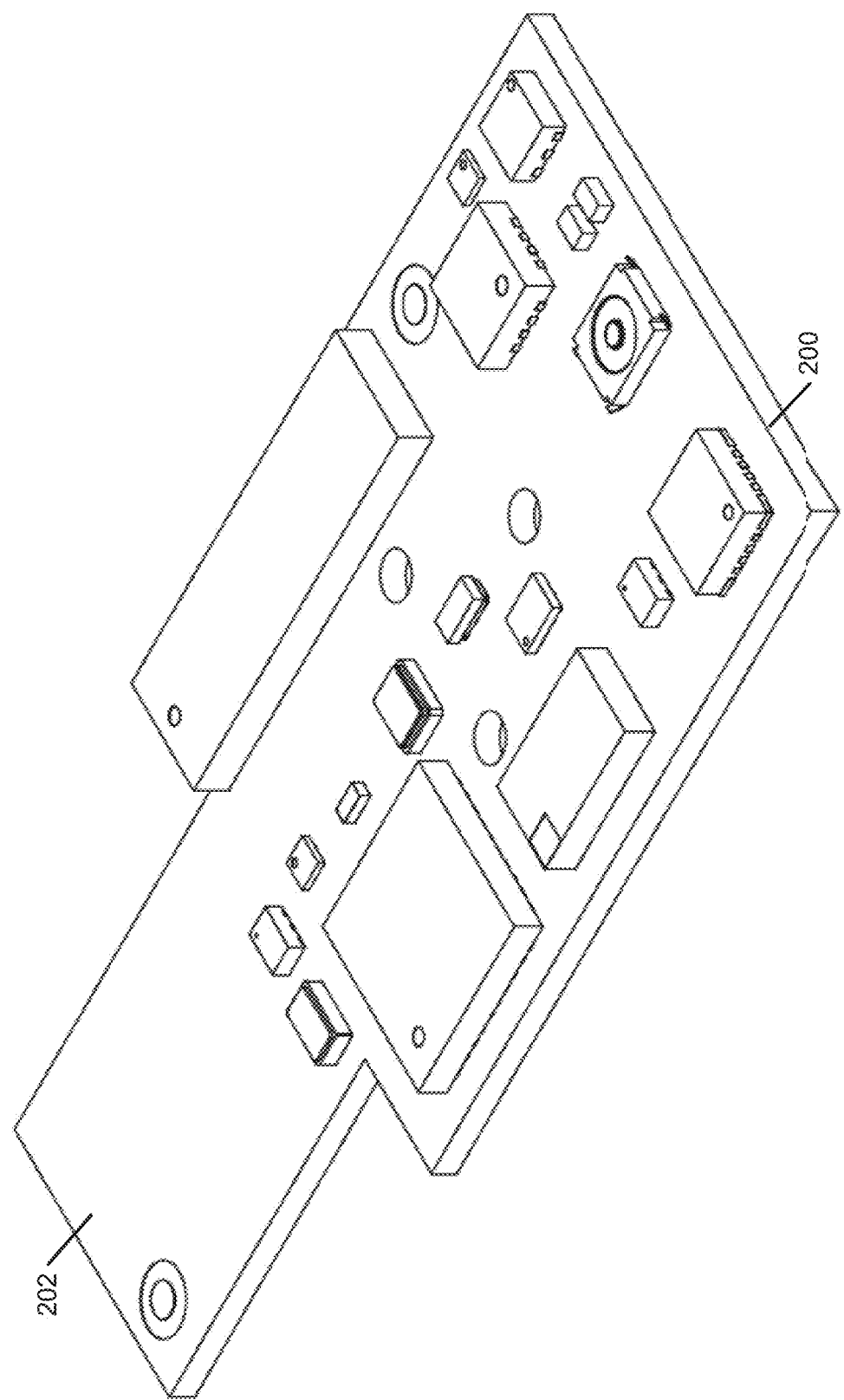

FIG. 2A is a top view diagram of an example printed circuit board assembly for a device to detect impact events. FIG. 2B is a side view diagram of an example printed circuit board assembly for a device to detect impact events. FIG. 2C is a bottom view diagram of an example printed circuit board assembly for a device to detect impact events. FIG. 2D is a front view diagram of an example printed circuit board assembly for a device to detect impact events. FIG. 2E is an isometric view diagram of an example printed circuit board assembly for a device to detect impact events. FIGS. 2A-2E illustrate the PCBA 200 including a male USB A connector 202.

Integrating the male USB A connector 202 into the PCBA 200 allows for a thin packaging solution with integrated communication and charging capabilities. In this example, the PCBA 200 is less than 1.6 mm in thickness. In contrast, other potential solutions include a micro-USB male connector, a micro-USB female receptacle that has a minimum of 2.80 mm on top of the PCB structure; a ⅛" (3.18 mm) female receptacle (headphone/microphone connection) has a minimum of 3.50 mm on top of a PCBA structure. The illustrated example using a male USB A connector 202 results in the thinnest non-proprietary connector integrated into the PCBA 200 with over-molding/pre-molding to allow it to fit properly into the respective female receptacle.

The male USB A connector 202 allows for connectivity with a wide variety of commonly available computing devices (e.g., laptops, desktops, tablets, etc.). The female counterpart is commonly integrated into PCs and Laptops, some tablets, cable connections to mobile device (phones and tablets), most new automobiles and other modes of transportation, extra battery packs, and wall plugs for charging USB devices. The male USB A connector 202 integrated into the PCBA 200 with a hard over-mold/pre-mold is extremely robust and easily manufactured. In an example, the male USB A connector 202 includes connector pins 204 (illustrated in FIGS. 2B and 2C in particular).

The PCBA 200 illustrated in FIGS. 2A-2E contains all essential electronic components for a functional impact detection device (dosimeter) except a power source (e.g., battery). Separation of the PCBA 200 and battery 304 creates a natural flex zone (illustrated in FIGS. 4A-4C as flex zone 406 and in FIGS. 5A-5E as flex zone 506).

PCBA and Battery Assembly

Figure 3C:
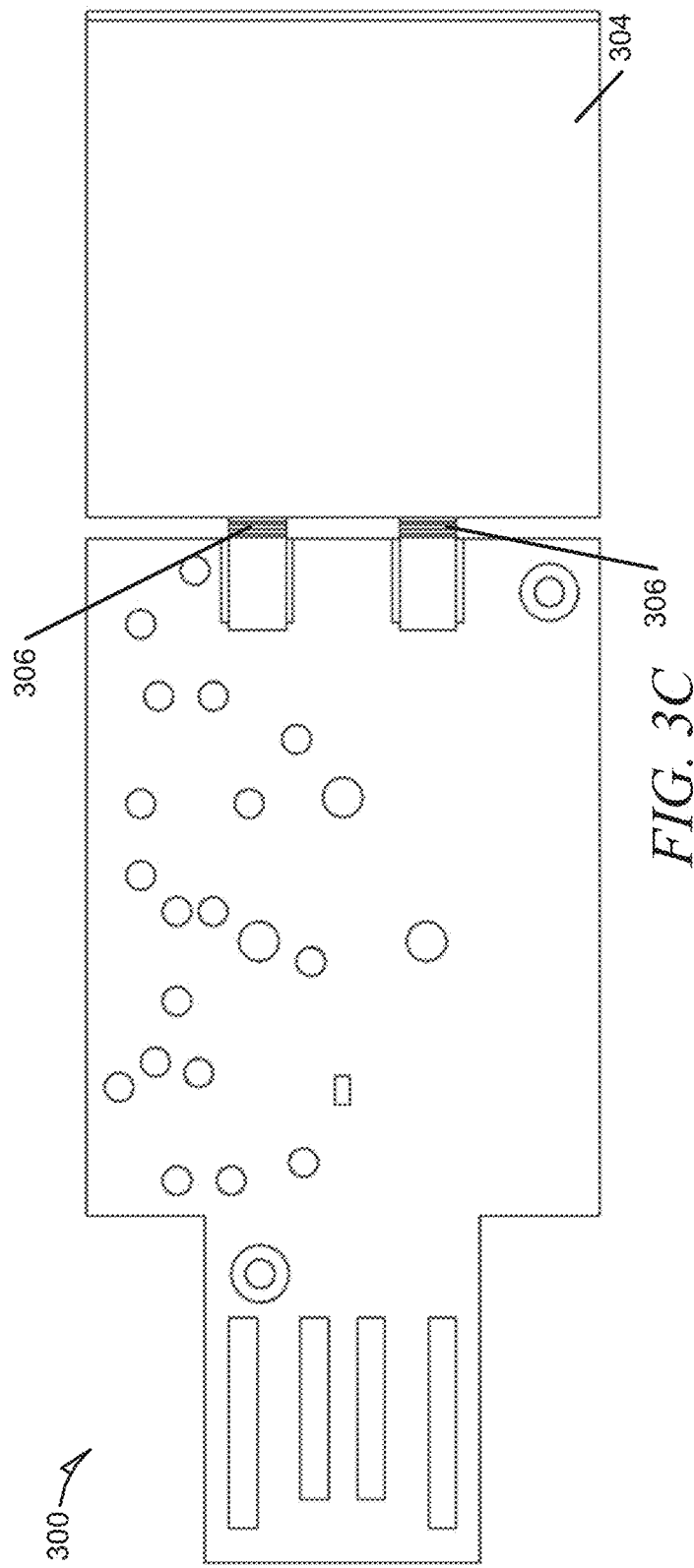
Figure 3D:
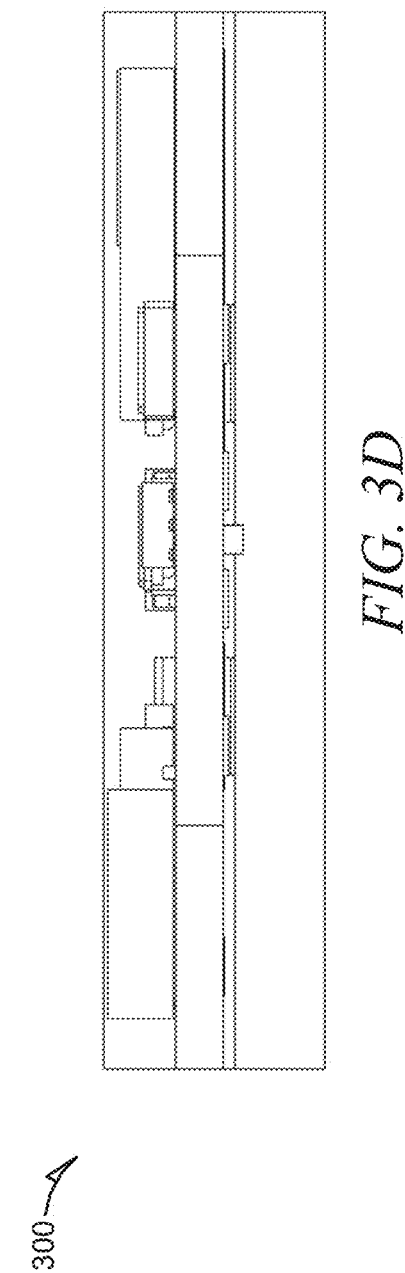
Figure 3E:
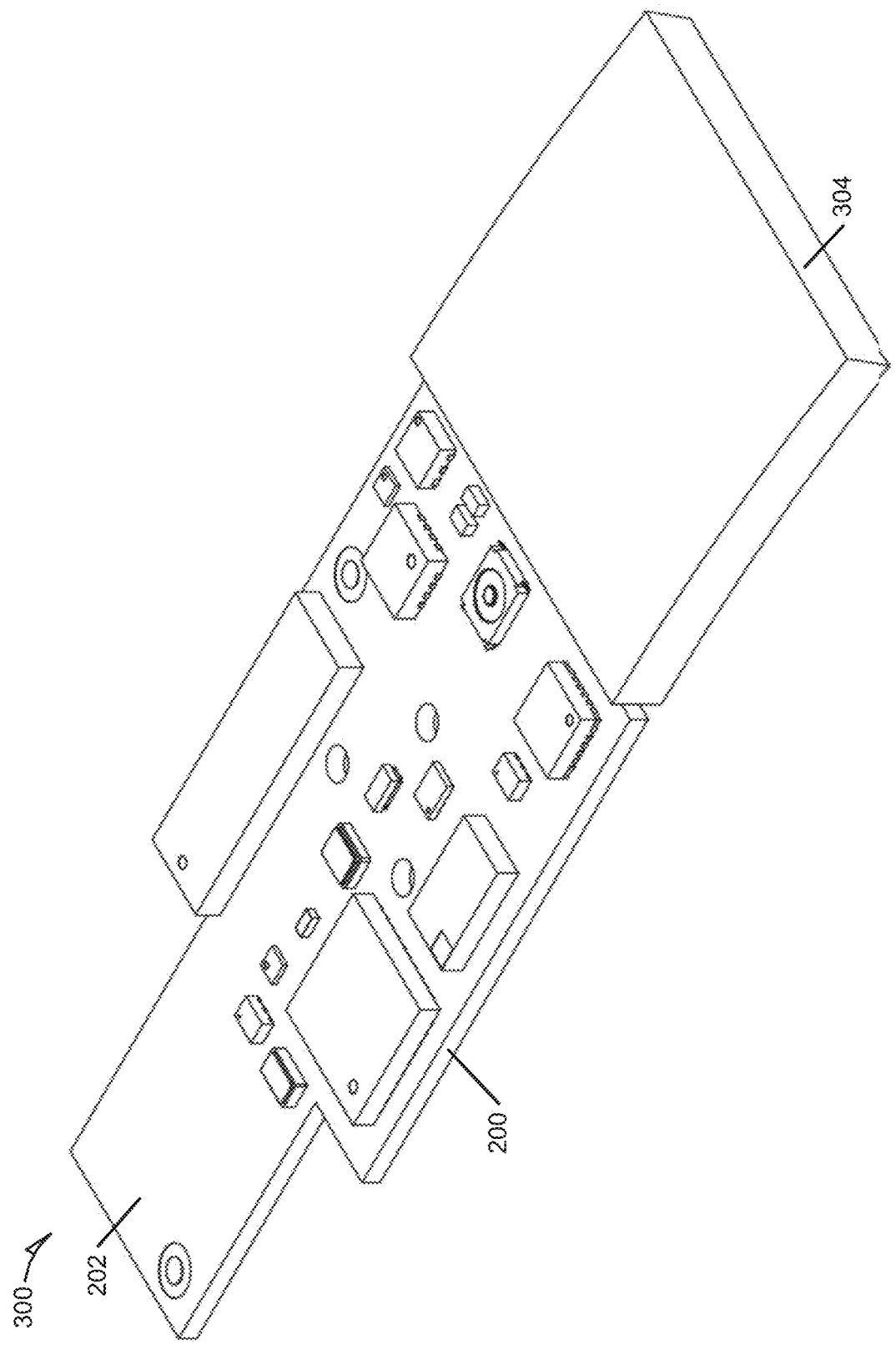

FIGS. 3A-3E are diagrams of an example printed circuit board assembly with a pre-bent battery attached prior to pre-mold. FIG. 3A is a top view diagram of the example PCBA and battery assembly 300. FIG. 3B is a side view diagram of the example PCBA and battery assembly 300. FIG. 3C is a bottom view diagram of the example PCBA and battery assembly 300. FIG. 3E is a perspective view diagram of the example PCBA and battery assembly 300. In these figures, a pre-bent battery 304 is electrically connected with the PCBA 200 prior to a pre-mold operation to seal and capture the PCBA and battery assembly 300. The battery connection 306 is formed to allow for flex between the battery 304 and the PCBA 200.

Pre-Molded PCBA and Battery Assembly

Figure 4E:
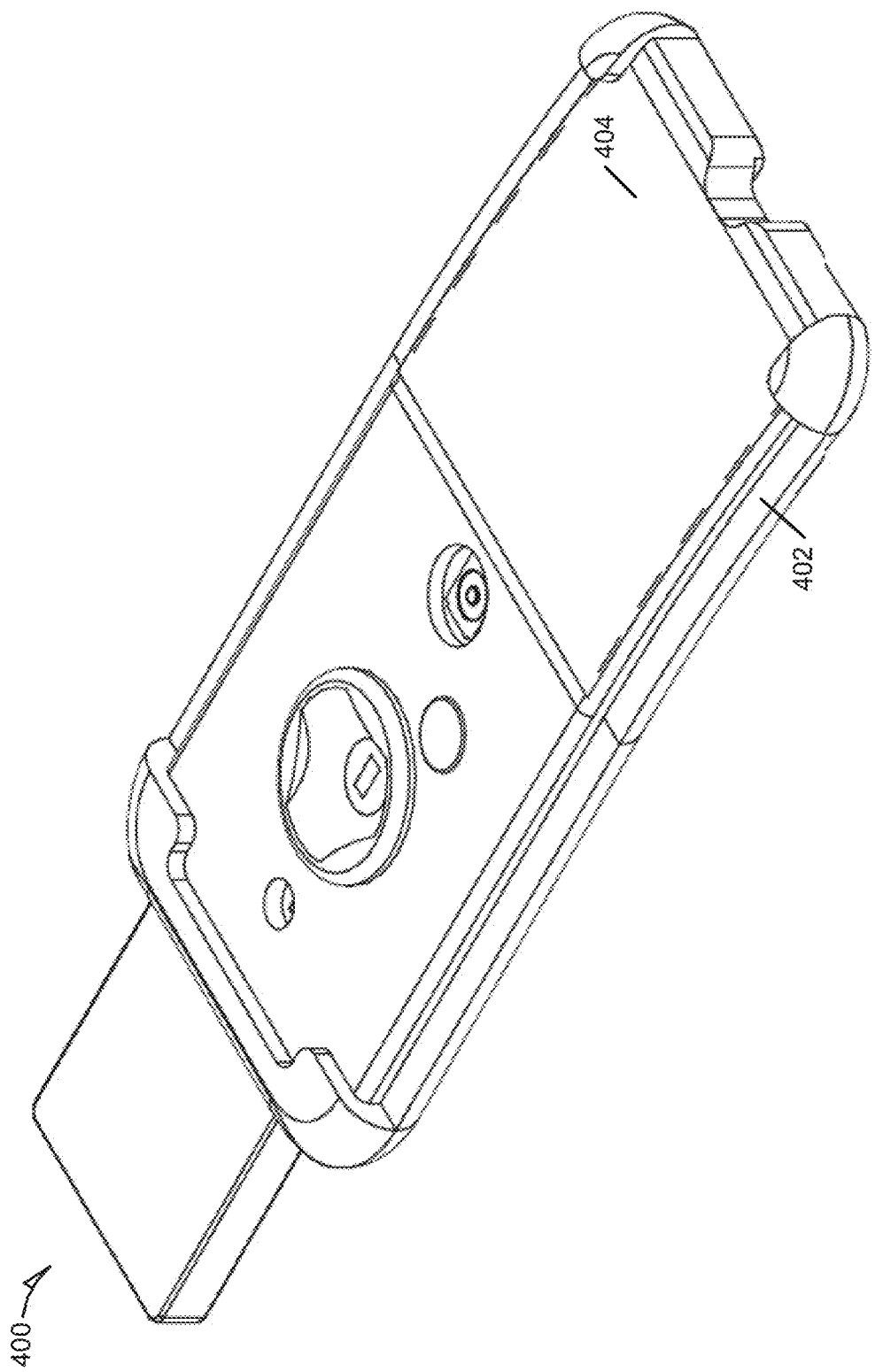

FIGS. 4A-4E are diagrams of an example pre-molded printed circuit board and battery assembly 400 with the battery 404 and surrounding pre-mold material forming a flexible cantilever section 402. FIG. 4A is a top view diagram of the example pre-molded PCBA and battery assembly 400. FIG. 4B is a side view diagram of the example pre-molded PCBA and battery assembly 400. FIG. 4C is a bottom view diagram of the example pre-molded PCBA and battery assembly 400. FIG. 4D is a front view diagram of the example pre-molded PCBA and battery assembly 400. FIG. 4E is a perspective view diagram of the example pre-molded PCBA and battery assembly 400. In this example, the pre-mold operation is utilized to form a cantilever section 402 that integrates the battery 404.

Hermetically Sealed PCBA—Pre-Molding

Figure 5C:
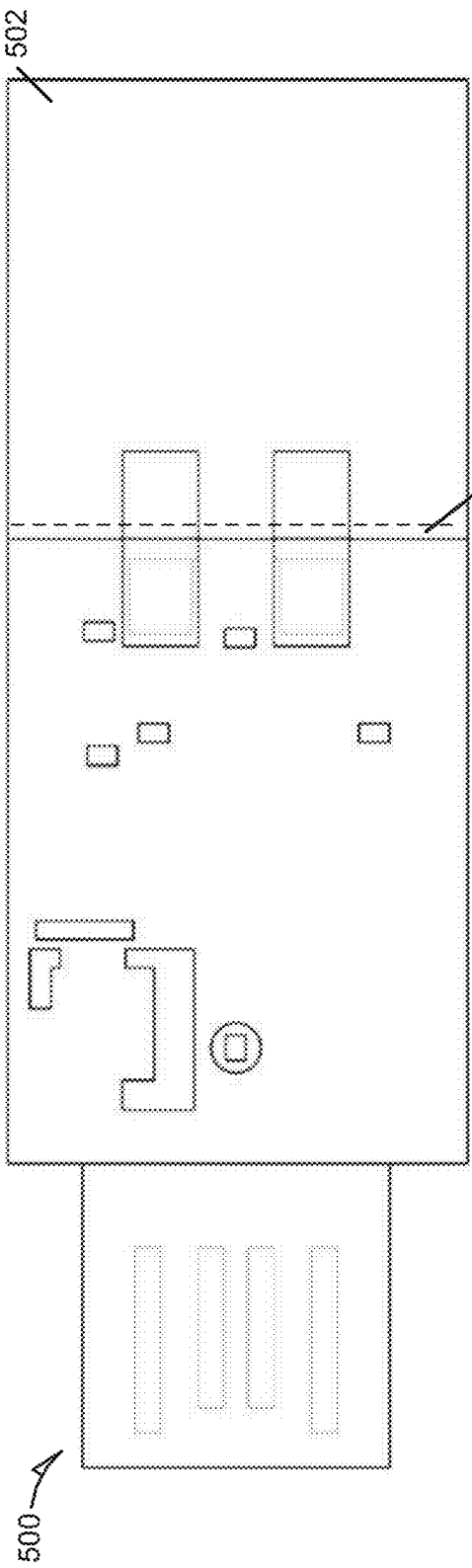
Figure 5D:
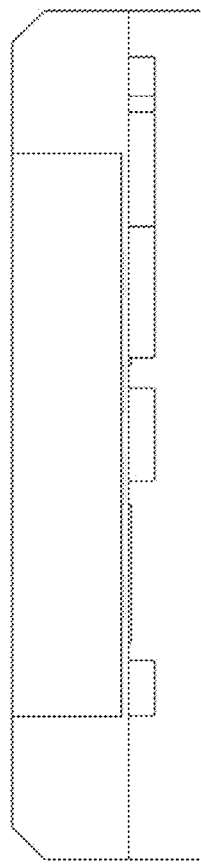
Figure 5E:
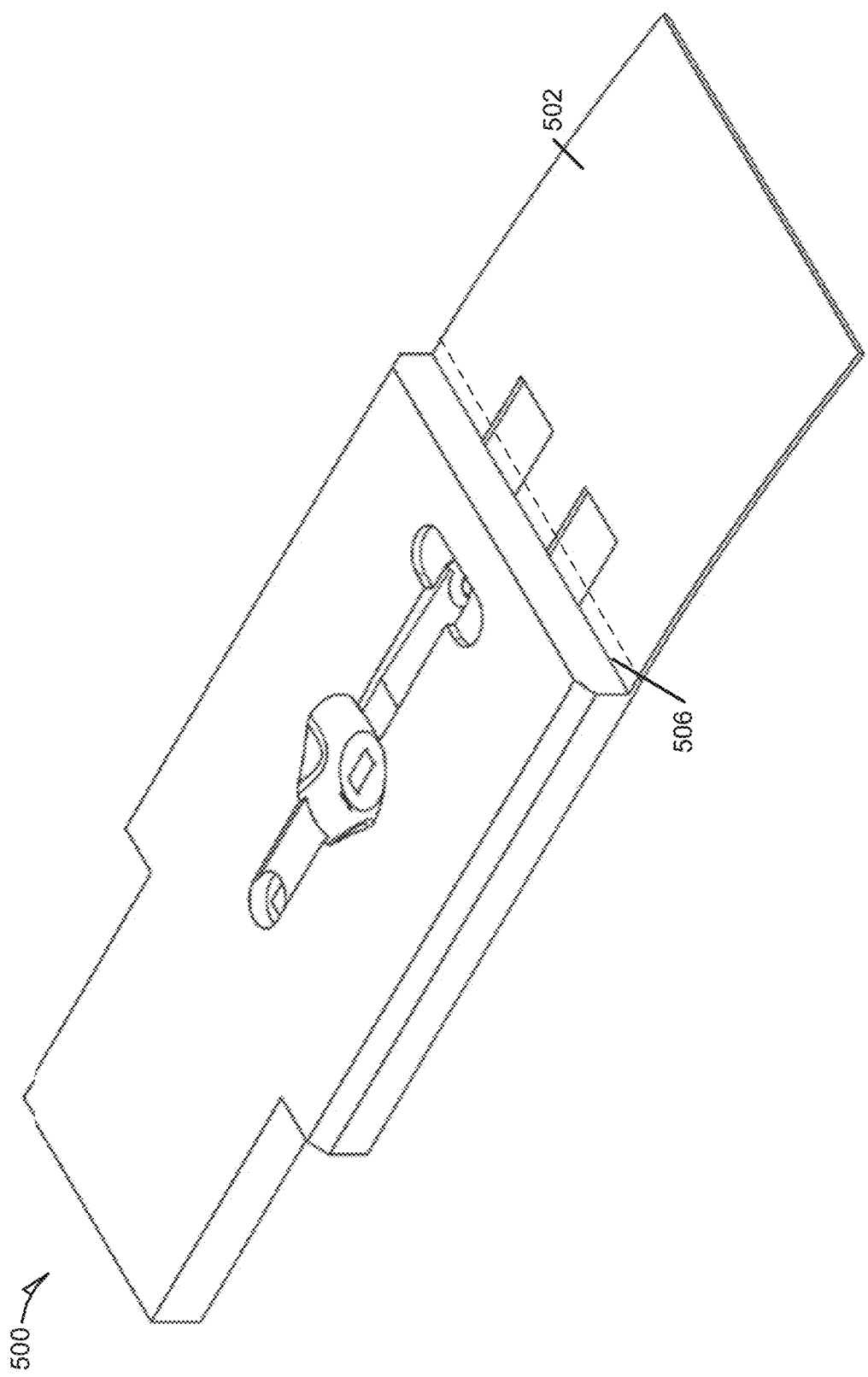

FIGS. 5A-5E are diagrams of an example partially completed impact detection device 500 including a pre-molded printed circuit board with a cantilever section 502 formed during pre-mold and ready to receive a battery. FIG. 5A is a top view diagram of an example hermetically sealed printed circuit board assembly for a device to detect impact events. FIG. 5B is a side view diagram of an example hermetically sealed printed circuit board assembly for a device to detect impact events. FIG. 5C is a bottom view diagram of an example hermetically sealed printed circuit board assembly for a device to detect impact events. FIG. 5D is a front view diagram of an example hermetically sealed printed circuit board assembly for a device to detect impact events. FIG. 5E is an isometric view diagram of an example hermetically sealed printed circuit board assembly for a device to detect impact events. Elements of the impact detection device 500 illustrated in FIGS. 5A-5E include a cantilever portion 502 that creates a controllable flex zone 506 between a battery and the PCBA 200 (not specifically illustrated in FIGS. 5A-5E).

In this and other examples, hard molding material can be used in the pre-molding operation to encapsulate all components of the PCBA 200 and protect them from vibration, blunt impact, shear forces, and other destructive forces. The pre-molding operation can provide an overall shape of the device to fit head contour. In an example, an injection moldable macromolecule polymer material can be used for the pre-molding operation. The pre-molding can hermetically seal all components that may become damaged by moisture, water, or other liquids. In some examples, the pre-molding in combination with the over-molding provides a hermetic seal for the electronic components.

FIGS. 5A-5E illustrate an example with a cantilever portion 502 molded to hold the battery (not shown). In another example, illustrated for example in FIGS. 4A-4E, the battery 404 can be encapsulated by the pre-molding (cantilever portion 402). These battery arrangements can provide strength to the overall device, strength to the flex zone to ensure the battery leads (306) and solder joints are not stressed, and allow an amount of flex to be varied according to application. The flexibility of a flex zone, such as flex zone 406 or 506, between the PCBA 200 and the battery 304 or 404 can be tuned based on material thickness, material properties, and mechanical design features.

The pre-mold can provide, along with the battery 304 or 404 (being bent), the curved shape of the device. It is desirable for the device to be naturally curved and flexible so that it can accommodate a wide variety of head shapes and alternative wearing locations on an end user. With natural differences in head shapes if the device does not flex it may cantilever tangent to the natural curve encountered in some wearing locations, which can impact measurement accuracy. It can also cause a smaller area of contact in which the device mounts to the head and can be more noticeable by the wearer because the force of the head mounting system and/or helmet.

Figure 6C:
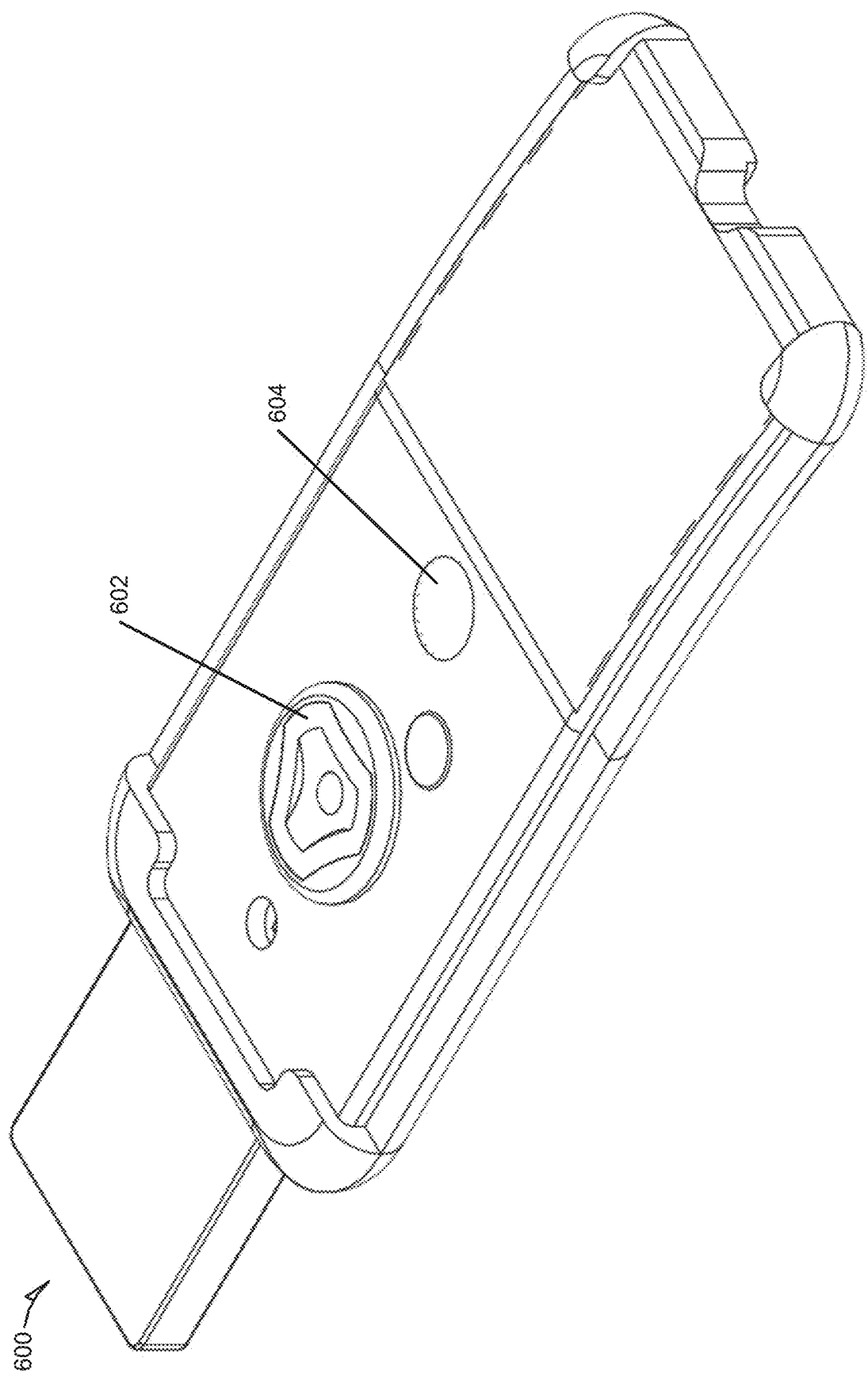

FIGS. 6A-6C are diagrams of a pre-molded impact detection device 600 with an example light pipe 602 and molded activation button 604. FIG. 6A is a top view diagram of an example hermetically sealed printed circuit board and battery assembly for a device to detect impact events. As mentioned above, these examples include a battery within the pre-mold, instead of creating a cantilever portion to hold the battery. FIG. 6B is a side view diagram of an example hermetically sealed printed circuit board and battery assembly for a device to detect impact events. FIG. 6C is an isometric view diagram of an example hermetically sealed printed circuit board and battery assembly for a device to detect impact events. In this example, these figures also illustrate a light pipe 602 and a molded in activation button 604.

Light Pipe

Figure 7C:
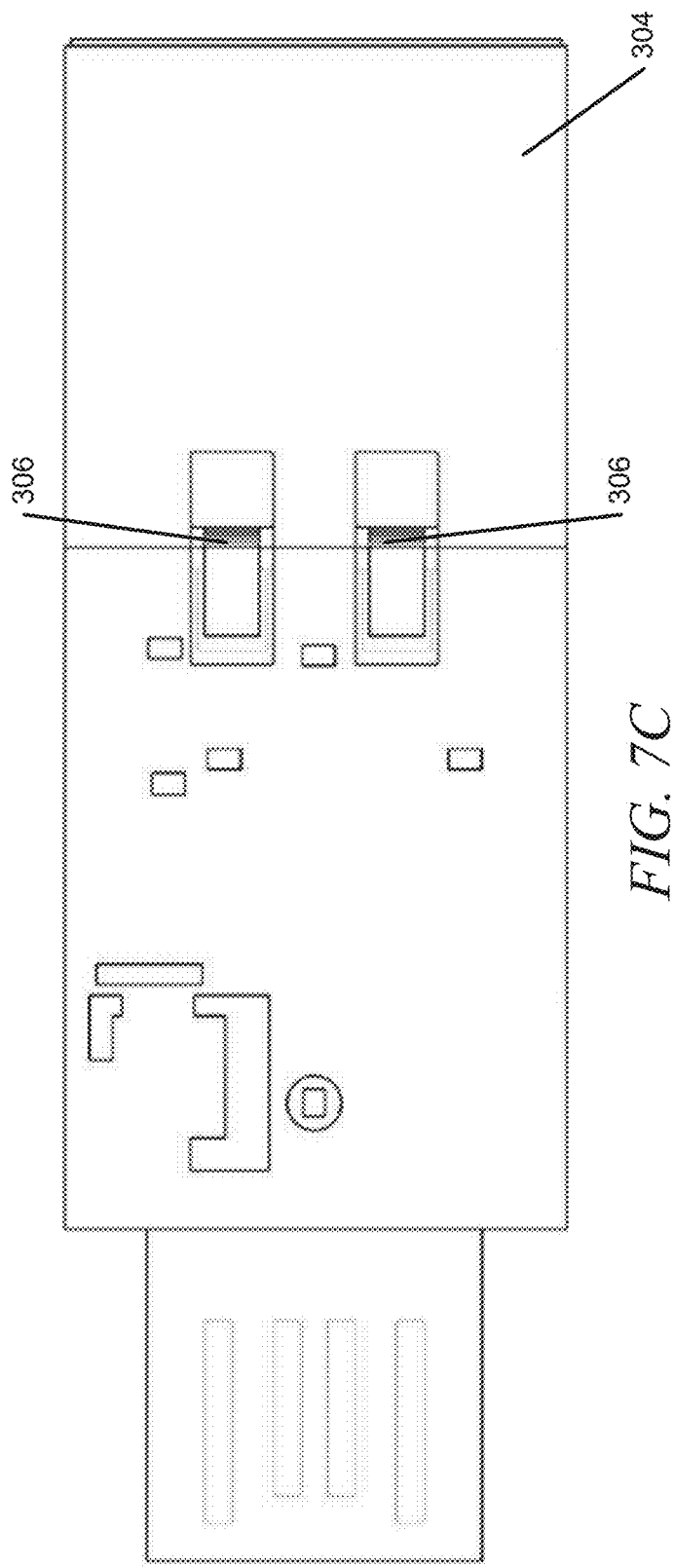
Figure 7D:
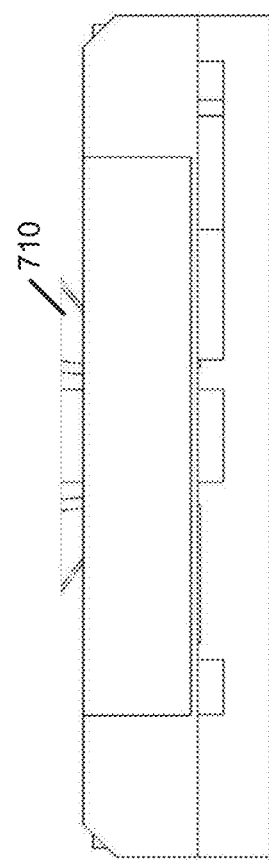

FIG. 7A is a top view diagram of a pre-molded impact detection device with an example light pipe 710 and button actuator 712. FIG. 7B is a side view diagram of a pre-molded impact detection device with an example light pipe 710 and button actuator 712. FIG. 7C is a bottom view diagram of a pre-molded impact detection device with an example light pipe and activation button. FIG. 7D is a front view diagram of a pre-molded impact detection device with an example light pipe 710 and button actuator. FIG. 7E is an isometric view diagram of a pre-molded impact detection device with an example light pipe 710 and button actuator 712. FIGS. 7A-7E also illustrate additional components of an example impact detection device, such as cantilevered section 502, battery 304, and flexible battery connections (leads) 306. In this example, the battery 304 is mounted on the cantilevered section 502, in other examples the battery 304 can be encapsulated when the cantilevered section 402 (not shown) is formed. The flexible battery connections 306 allow for flexure between the PCBA and the battery 304.

The light pipe 710 can be a coated transparent structure with openings in coating for light input/output forcing input light to undergo reflections sufficient to mix and uniformly distribute multiple sources to produce an output. The light pipe 710 can be circularly symmetric with a light source at the center. A hemisphere can be included above the light sources to provide a reflecting surface. The light pipe 710 includes metallized coating for reflection, removed at top and bottom planar surfaces. In an example, the hemisphere positioned over the LEDs to direct light into a circularly symmetric structure with engineered inner and outer surface geometries that provide mixing and uniform illumination in a vertically constrained environment. In certain examples, the hemisphere, diameter and height, can be varied to achieve the desired level of light mixing. Light sources used with the light pipe 710 can include more than one source with different spectral characteristics. In one mode, a single LED can be used (turned on) for a uniform single color. In another mode, multiple LEDs can be used (turned on) for uniform color mixing. FIGS. 9A-9E illustrate an alternative light pipe design isolated from the example impact detection device structure.

Figure 9C:
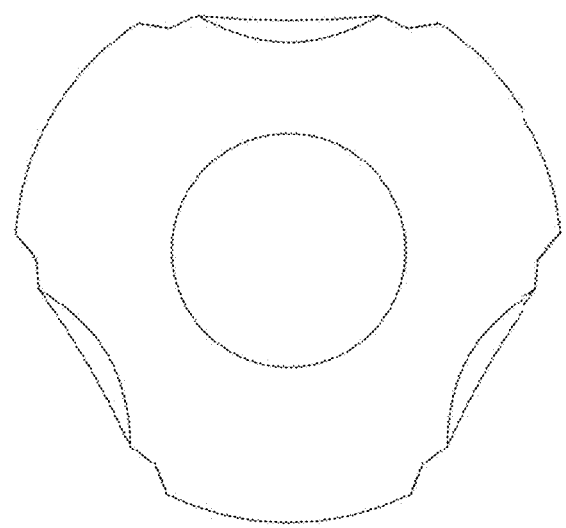
FIGS. 9A-9E are diagrams of an example light pipe without the reminder of the impact detection device.
Figure 9D:
Figure 9E:
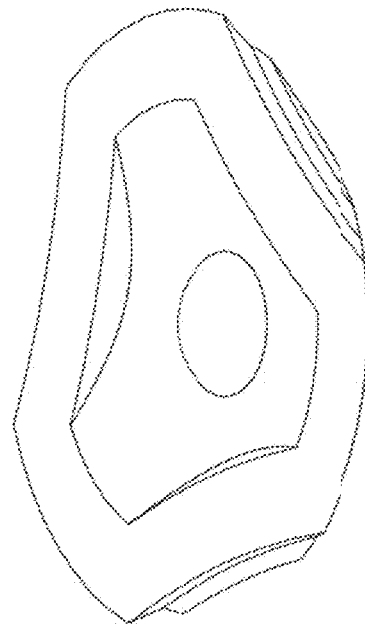
Figure 9A:
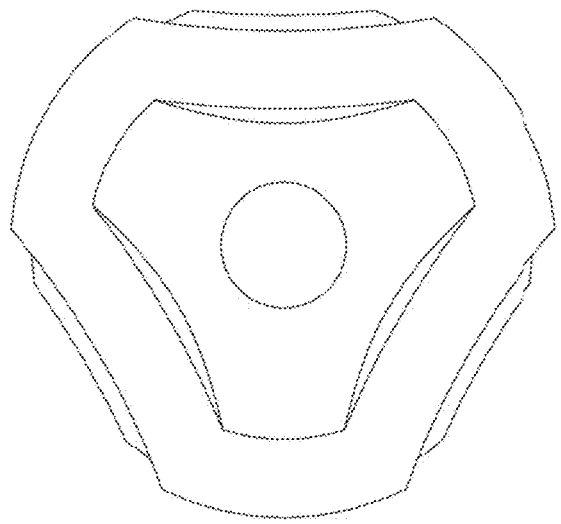
Figure 9B:
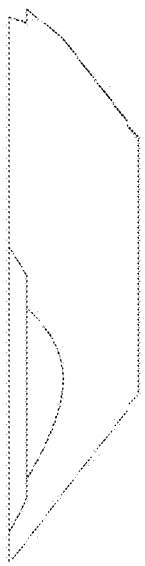

FIG. 9A is a top view diagram of an example light pipe without the reminder of the impact detection device. FIG. 9B is a side view diagram of an example light pipe without the reminder of the impact detection device. FIG. 9C is a bottom view diagram of an example light pipe without the reminder of the impact detection device. FIG. 9D is a front view diagram of an example light pipe without the reminder of the impact detection device. FIG. 9E is an isometric view diagram of an example light pipe without the reminder of the impact detection device.

The light pipe can provide a method to distribute illumination provided by LEDs through semi-translucent over-mold materials and can integrate an activation button (see FIG. 7A button actuator 712). The light pipe can enable color mixing to achieve an array of colors from a limited number of LEDs (e.g., red and green). Light pipes can also be adapted to display trademarks or logos.

Over-Molded Final Assembly

Figure 8C:
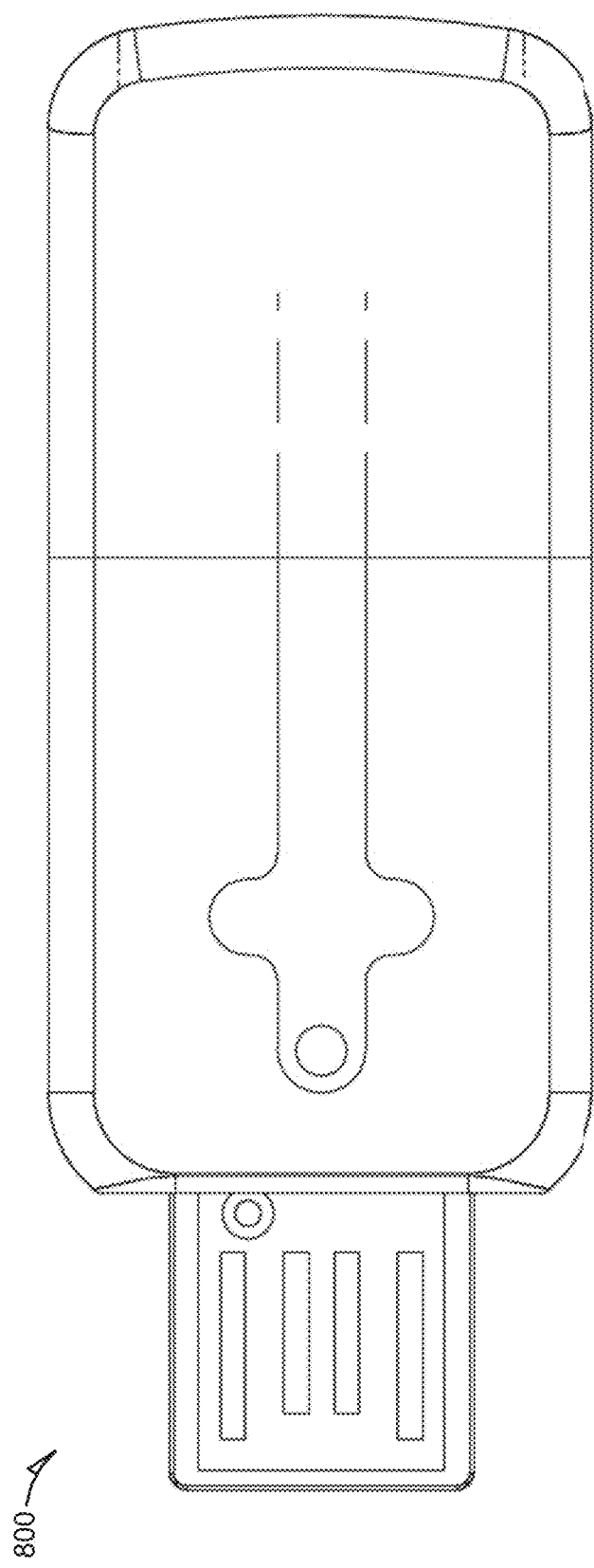
Figure 8D:
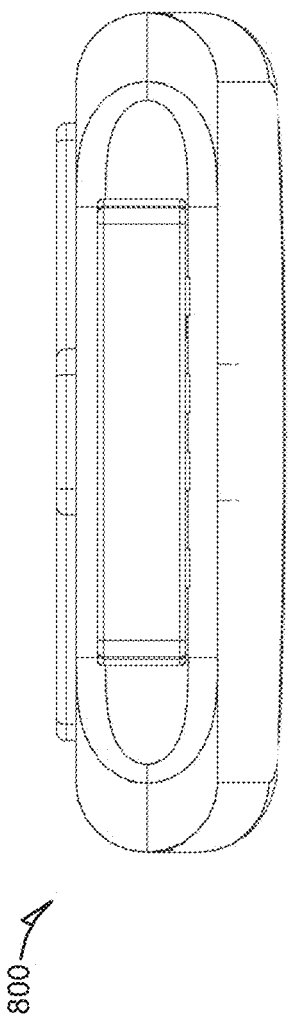
Figure 8E:
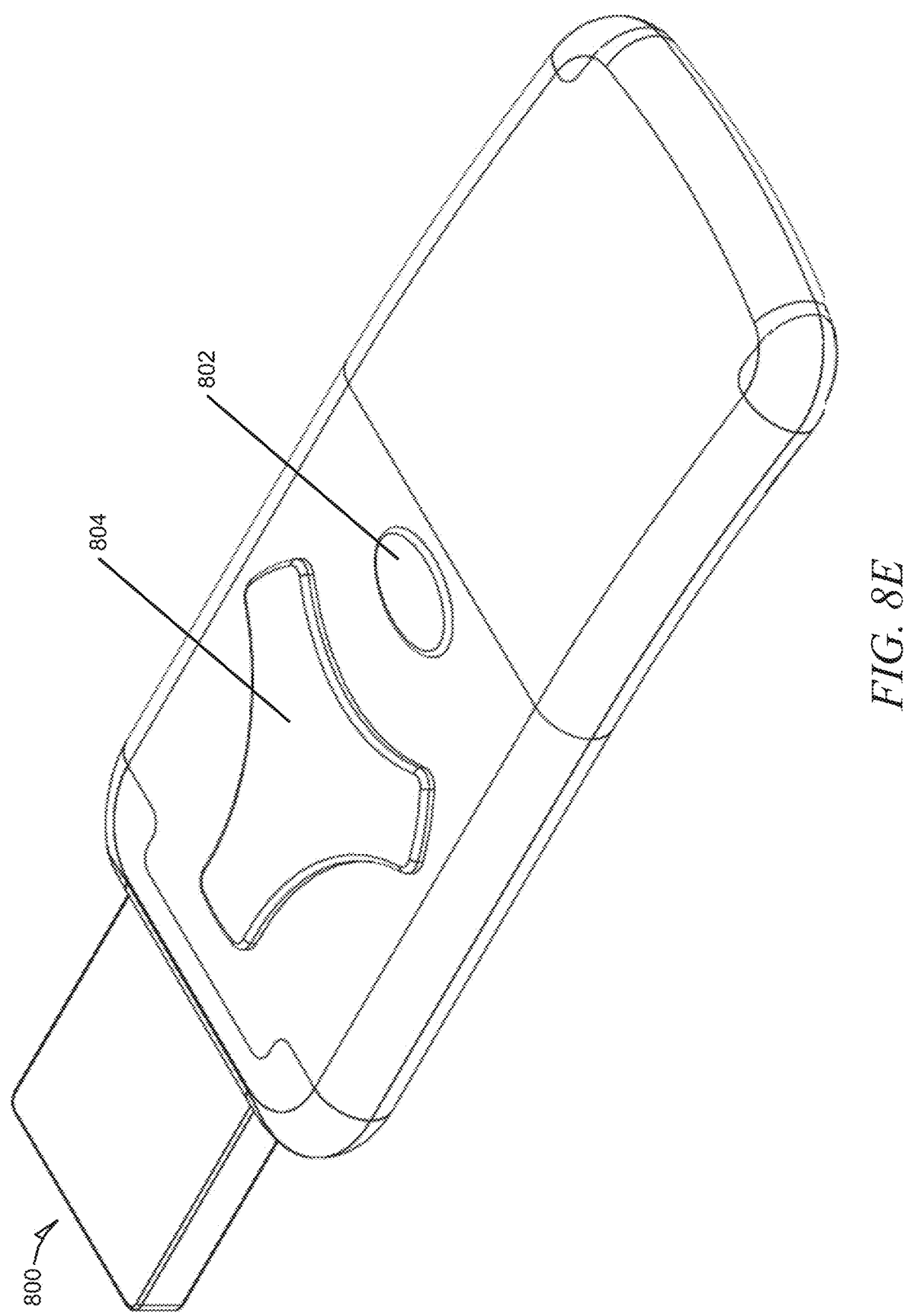

FIGS. 8A-8E are diagrams of an example over-molded impact detection device 800 with molded activation button 802 and translucent light pipe covering 804. FIG. 8A is a top view diagram of an example impact detection device 800 with a final soft over-mold. FIG. 8B is a side view diagram of an example impact detection device 800 with a final soft over-mold. FIG. 8C is a bottom view diagram of an example impact detection device 800 with a final soft over-mold. FIG. 8D is a front view diagram of an example impact detection device 800 with a final soft over-mold. FIG. 8E is an isometric view diagram of an example impact detection device 800 with a final soft over-mold. In this example, the diagrams illustrate a translucent portion 804 of the over-mold covering the light pipe as well as a molded-in activation button 802. In this example, the over-mold provides translucence for illumination from the LED sources through the material. The over-mold does can be selected to limit impact on the spectral characteristics of the emitted light. Alternatively, the spectral characteristics (e.g., mixing) of the light source can be adjusted to account for any impacts of the over-mold on the emitted light. The over-mold also appears opaque until illuminated by the internal light sources (e.g., LEDs).

The final over-mold material can provide a comfortable feel for user while both wearing and handling the device. The final over-mold can also give definition to the overall device. In certain examples, the final over-molded impact detection device can include features to assist in securing the device within a head mounting system (e.g., a head band or a skull cap, among others). The figures do not include specific features for securing the device within the head mounting system. Finally, the over-mold material and process is designed to provide an extra layer of moisture, water, and other chemical resistance.

Example Monitoring and Evaluation Interfaces

FIG. 10A is an illustration of an example web-based dashboard interface 1000 for monitoring users of an impact detection device. The interface 1000 can include multiple information areas or zones for display and interaction with data generated from one or more impact detection devices. In an example, the interface 1000 can include information zones such as: an activity and impact timeline 1005, an Impact Assessment System (IAS) score 1010, impact metrics 1015 including the HIC score, maximum linear acceleration, maximum rotational acceleration and maximum rotational velocity among others, an alert section 1020, highest IAS score today 1021, hit count 1022, an impact area illustration 1025, an impact vector indicator 1027, a impact data graph 1030, and a hit recovery section 1040. The hit recovery section 1040 can include a recovery test button 1045 that can initiate an interactive survey to evaluate a player's cognitive functions, among other things. In an example, the interactive survey can include all or a portion of a SCAT3 assessment. The impact timeline 1005 can use a bar graph to illustrate time-stamped impact events. The impact timeline 1005 can be scaled in various time increments depending upon available data or user preferences. The impact timeline 1005 can display historical data or impact events as they occur or both. In an example, selecting a bar or event within the impact timeline 1005 can display details regarding the selected event or group of events. The impact area illustration 1025 can provide a graphical illustration of where the detected impact occurred on a player's head, or an axis of rotation. For instances where devices are worn on the torso and head, the illustration can be expanded to include location of torso hits coupled with resulting head acceleration vectors. In certain examples, the impact area illustration 1025 can include an animation illustrating one or more impact events. The impact viewer can also include an impact vector indicator 1027 that can provide information on the direction of rotation imparted to the body during the recorded impact.

The IAS score 1010 provides a numeric estimation of the magnitude of the detected impact on a numeric point scale. In an example, the IAS score 1010 can represent a scoring system that translates any injury metric curve to a quantized set of values. The IAS point scale translates to any injury risk curve by quantizing the scale based upon percent likelihood of injury, which allows for future adaptation of the algorithm while maintaining a consistent scale. For example, values can be based upon the percent likelihood of injury. The injury metric curve can be broken up into sections based upon the percent likelihood of injury. Each section is given part of a continuous range. This range maps the percent likelihood of injury to a set of values that are independent of the metric used to calculate the percent likelihood of injury. In other examples, a different scale can be used, multiple scales can be combined, or an actual force measurement can be provided. In certain examples, a piecewise linear curve with higher sensitivity for low level hits can be used to enable a user to distinguish between low-level impacts, such as may be encountered during training sessions. Traditional impact metrics have a tendency to zero out low-level impacts, reducing the ability to use these metrics for things like training.

The HIC score listed in impact metrics 1015 is the Head Injury Criterion, which is a measure of the likelihood of injury from an impact based upon acceleration sustained over time. The highest IAS score today 1021 highlights the biggest impact recorded that day (or in any configurable timeframe). Hit count 1022 can indicate the number of hits received over a specified period of time by the particular player. The alert section 1020 can list event or other information a user may be interested in, such as high count of hits in one time period or biggest impact on record.

FIG. 10B is an enlarged illustration of an example impact data graph 1030 portion of the interface 1000 illustrated in FIG. 10A. As illustrated in FIG. 10B, the Impact Data graph 1030 can include measurements provided by sensors within the impact detection device and/or calculations performed based on measurements. In this example, X-axis, Y-axis, and Z-axis rotations are depicted along with the resultant magnitude.

Figures 11A, 11B:
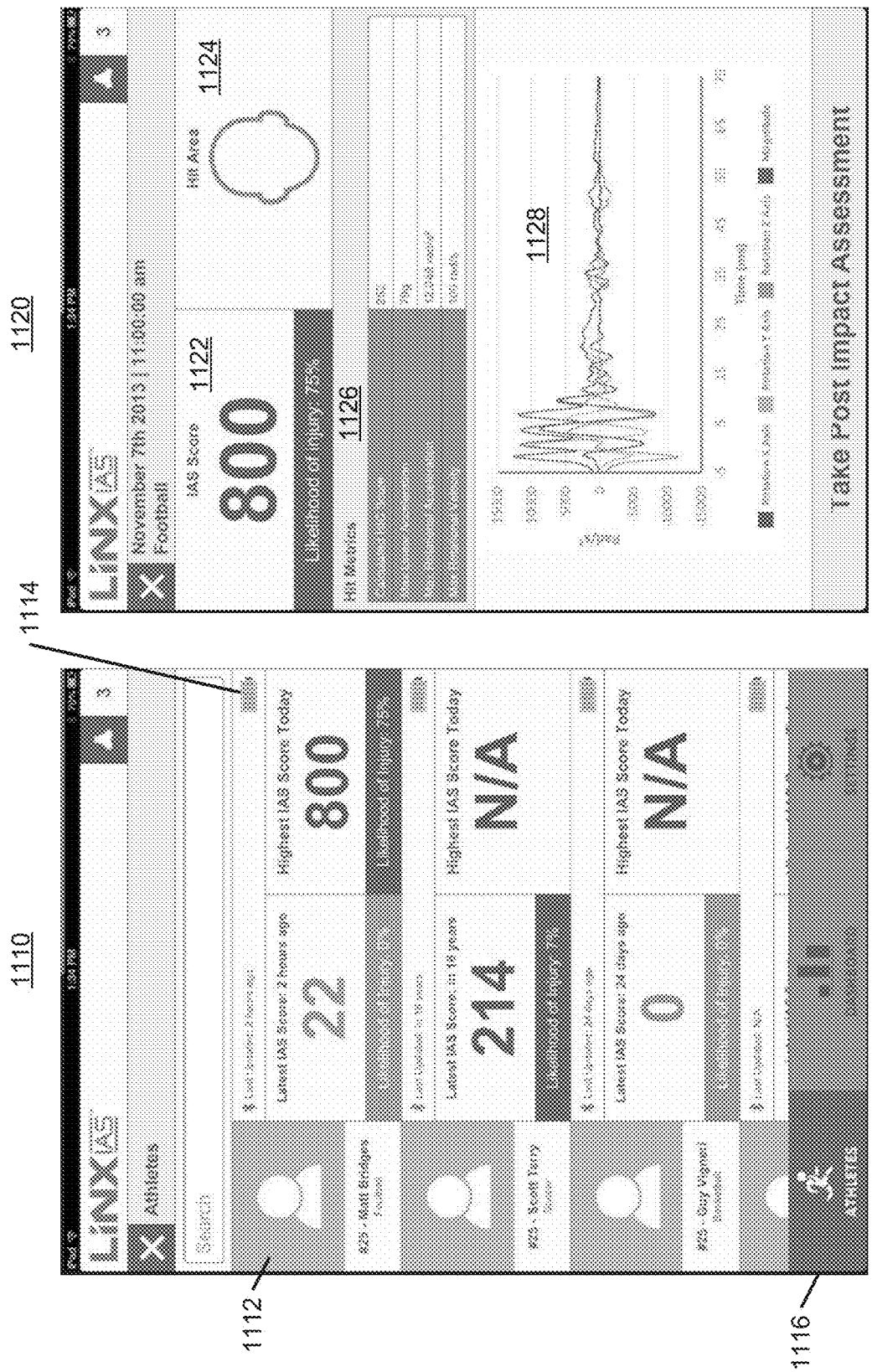
FIGS. 11A-11D are illustrations of multiple example mobile device user interface screens for monitoring users wearing impact detection devices.

FIGS. 11A-11D are illustrations of multiple example mobile device user interface screens for monitoring users wearing impact detection devices. The interfaces illustrated in FIGS. 11A-11D include interactive information zones for displaying and manipulating data generated by one or more impact detection devices. The interactive information zones are responsive to user input that can vary based on the type of mobile device being used (e.g., touch input versus cursor-based input). FIG. 11A illustrates user interface 1110 that illustrates an example interface depicting data for multiple team members with various information graphics and icons providing present and historic data. In an example system, the interface 1110 can be generated by a mobile application accessing a network-based server collecting and maintaining data across the multiple team members. In another example, the mobile application generating interface 1110 can also receive data directly from impact detection devices over a wired (e.g., USB) or wireless (e.g., Bluetooth) communication interface. Data received directly from impact detection devices can also be synchronized by the mobile application with a network-based server. User interface 1110 can include interface elements such as player display 1112 that can include Latest IAS Score and Highest IAS Score displays and impact detection device status indicator 1114. The impact detection device indicator 1114 provides indications such as last connection time and battery status, among other things. The user interface 1110 can include navigation buttons 1116 that allow navigation between different user interfaces illustrated in FIGS. 11A-11D. In another example, the interface 1110 (as well as interfaces 1120 and 1130) can be generated from data collected by the mobile device directly from one or more impact detection devices. FIG. 11B illustrates user interface 1120 that illustrates an example individual player interface on a mobile device. The interface 1120 can include additional data on the individual players and an enlarged view of the information depicted in interface 1110. In this example, interface 1120 includes elements such as an IAS Score 1122 display, a Hit Area display 1124, a Hit Metrics display 1126, and an impact data display 1128. The displays on interface 1120 correspond to displays discussed in reference to FIG. 10A. The interface 1120 within the impact data display 1128 can depict actual output from an accelerometer or gyroscope over a period of time. The illustrated period of time can include an impact event to assist in visualizing the extent of the impact.

Figure 11C:
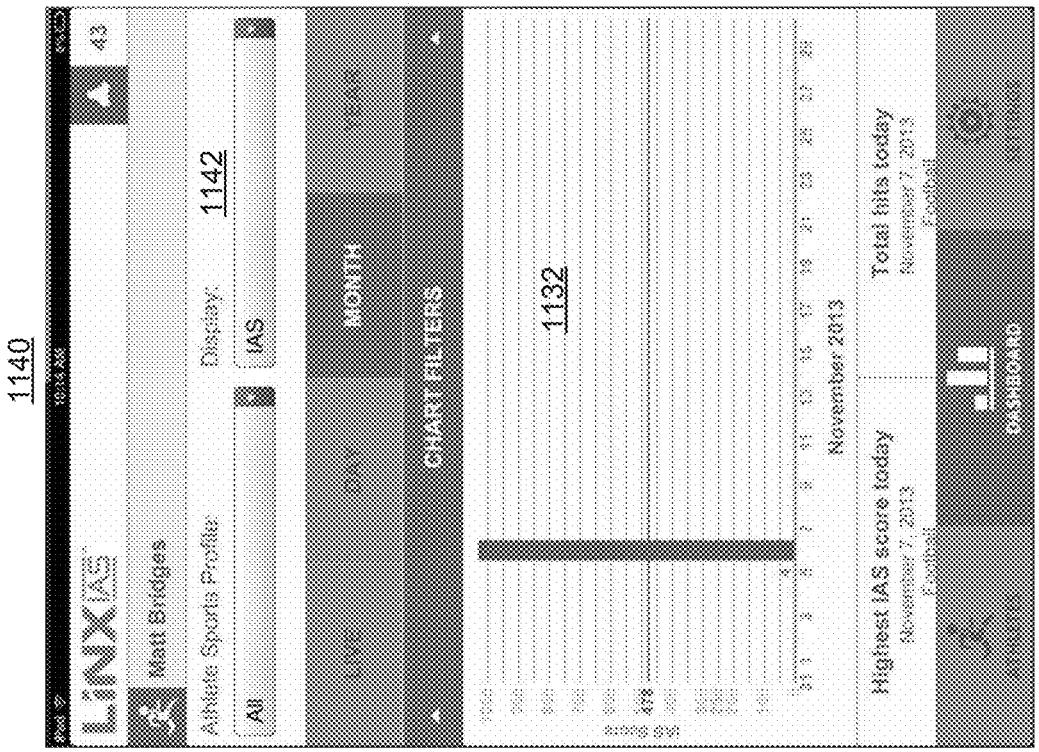
Figure 11D:
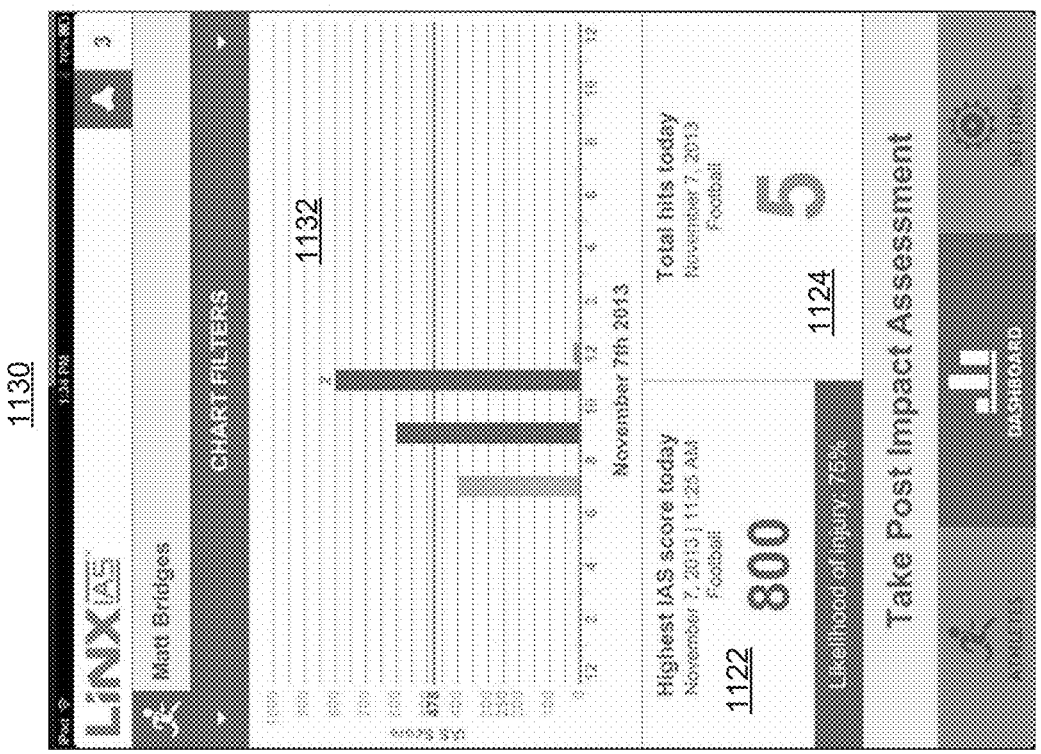

FIGS. 11C and 11D illustrate user interfaces 1130 and 1140 that provide additional example displays for individual player data. For example, interfaces 1130 and 1140 include histogram display 1132 that can display time stamped IAS score data over a period of time. Interface 1140 illustrates chart filters 1142 that enable filtering of the data displayed in histogram display 1132.

Example Evaluation Methods

Figure 13:
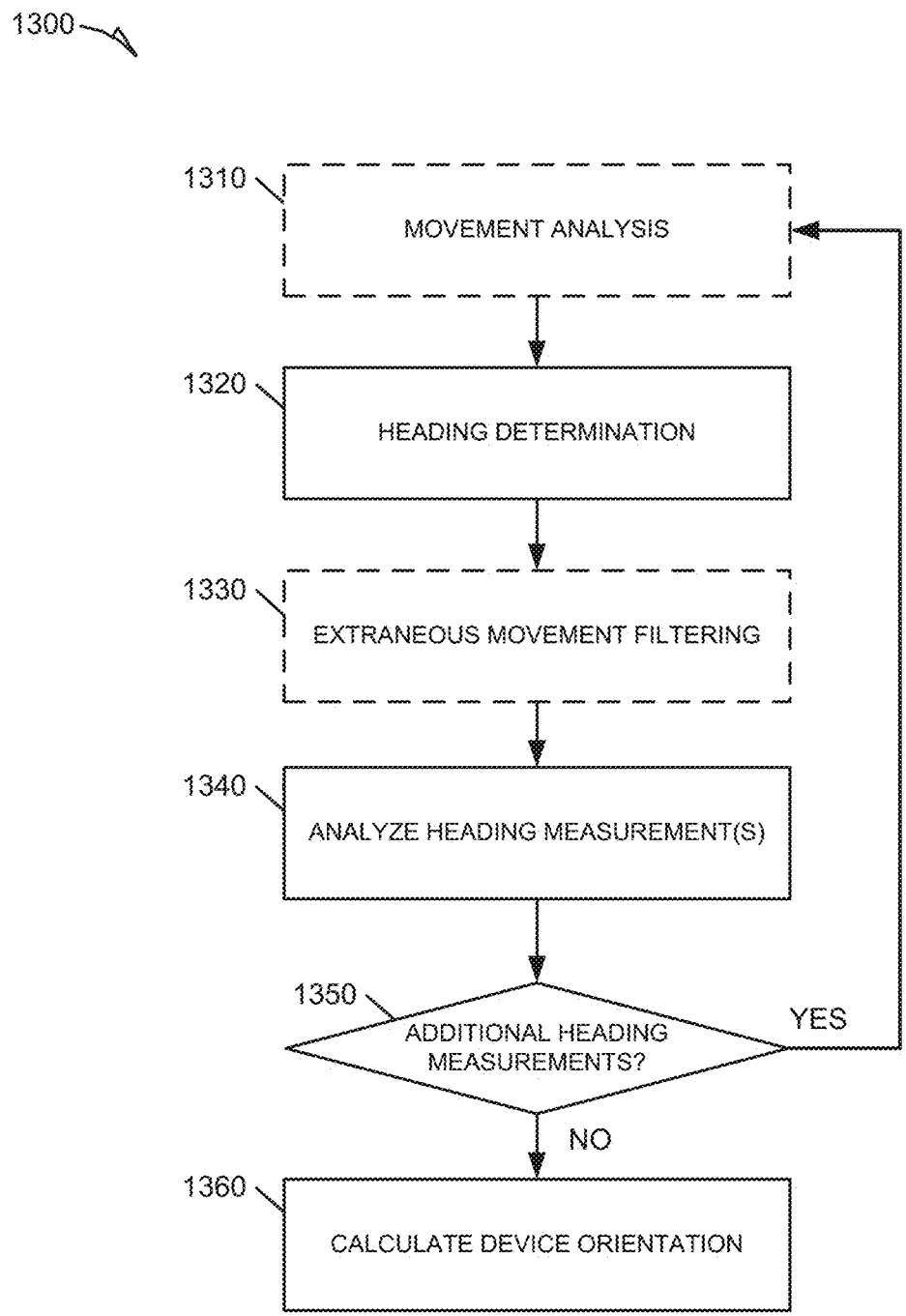
FIG. 13 is a flowchart illustrating an example method for determining position and orientation of an impact detection device worn by a user.

FIG. 13 is a flowchart illustrating an example method 1300 for determining an orientation and location of an impact detection device worn by a user. In an example, the method 1300 can include operations such as: analyzing movement of a user wearing an impact detection device at 1310, determining a heading of the user at 1320, filtering out extraneous movements of the user (e.g., head movements and movements associated with walking) at 1330, determining whether additional heading measurements should be gathered at 1350, and calculating a device orientation with respect to the user at 1360. The method 1300 can be performed on-board an impact detection device, such as impact detection device 100, or on an offline computing system with data obtained from impact detection device 100. The following example is discussed as occurring on-board the impact detection device 100.

In an example, the method 1300 can begin at 1310 with the impact detection device 100 analyzing movement of a user wearing the impact detection device 100. The impact detection device 100 can obtain and analyze inputs such as gait and frequency of movement to determine when the user is walking. During periods of sustained movement, such as walking, the method 1300 can continue at 1320 with the impact detection device performing a heading calculation based upon acceleration vectors gathered by sensors within the impact detection devices, such as a 3-axis accelerometer 112. At 1330, the method 1300 can continue with the impact detection device 100 using the gyroscope 110 to filter out extraneous movement, such as movements associated with the head turning. The impact detection device 100 can gather a heading measurement periodically whenever a walking pattern is detected in order to improve the accuracy and remove any erroneous calculations from the heading estimate. At 1350, the method 1300 can optionally include a decision point to determine if additional heading measurements need to be gathered. If additional heading measurements are desired, then method 1300 can loop back to operation 1310. In certain examples, statistical methods and confidence weight can be applied to new data as it is added to the dataset. In an example, results of the movement calculations can be stored within memory 108. At 1360, the method 1300 can conclude with the impact detection device 100 calculating a device orientation in reference to a center of gravity of a user, or some other reference point.

Figure 12:
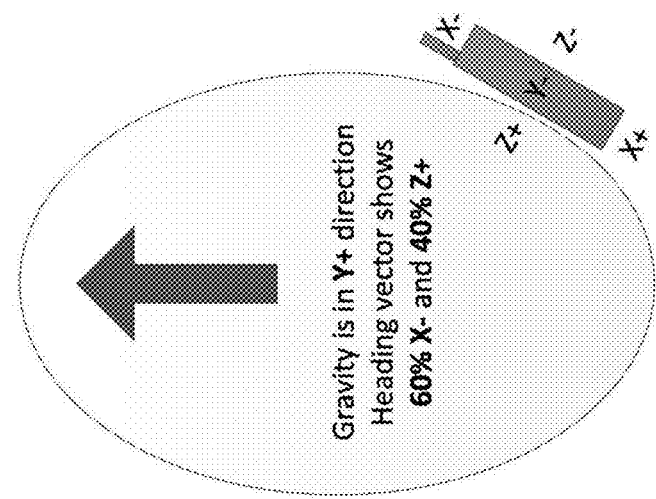
FIG. 12 is an illustration of multiple example orientation detection scenarios for determining orientation of an impact detection device.
Figure 12:
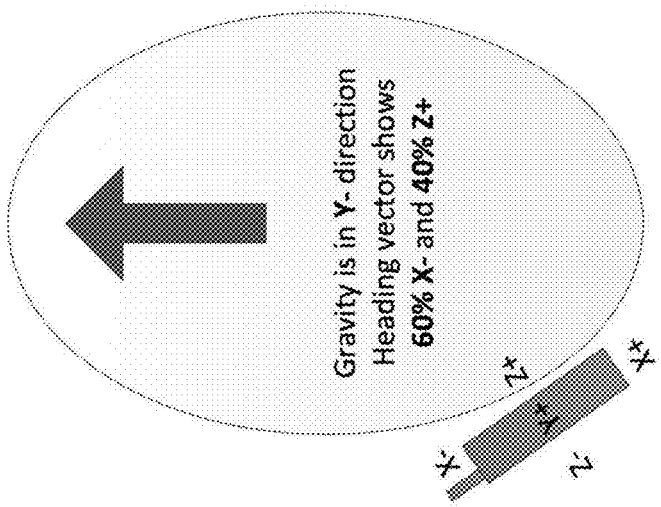
Figure 12:
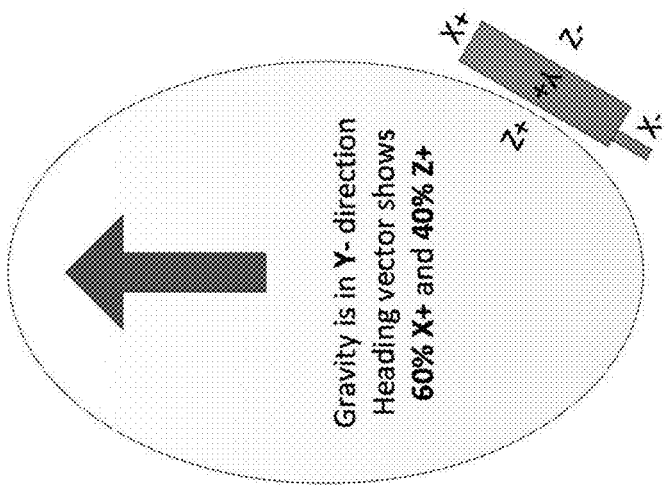

FIG. 12 illustrates multiple example orientation scenarios that can be determined with method 1300. Once the heading is known it is used in conjunction with the gravity vector to determine the orientation of the sensor. An illustration of this concept is provided in FIG. 12.

Case 1: The user places the sensor behind their right ear with USB pointing clockwise.
  Gravity vector: Y−
  Heading vector X: X+ 600
  Heading vector Z: Z+ 40%

Case 2: The user takes sensor off and places it back on rotated clockwise to behind the back left ear with USB pointing clockwise.
  Gravity vector: Y–
  Heading vector X: X– 60%
  Heading vector Z: Z+ 40%

Case 3: User rotates device so that the USB is now pointing counter-clockwise and places it back behind the right ear.
  Gravity vector: Y+
  Heading vector X: X– 60%
  Heading vector Z: Z+ 40%
  Additional Evaluation Algorithms:

Adaptive thresholds based on network-based (e.g. cloud) data and concussion history of individual. In an example, the impact event history and medical history for an individual can be used to adaptively modify thresholds related to event capture triggering, indicator light operation, and the injury risk assessment score. Adaptive thresholds can be based on time-weighted sums of individual event severity or injury risk assessment scores, with more recent event weighted more heavily than older events. In some examples, the sideline and post-game assessments, as compared to the baseline, can also impact the adaptive thresholds. Established and evolving return to play criteria can be utilized in conjunction with adaptive thresholds.

Event detection using combination of linear and rotational acceleration. In an example, various combinations of the following measurement criteria can be utilized as trigger criteria for event detection:
  Linear acceleration exceeding a threshold
  Linear acceleration exceeding a threshold for a set duration of time
  Rotational velocity exceeding a threshold
  Rotational velocity exceeding a threshold for a set duration of time
  Rotational acceleration exceeding a threshold
  Rotational acceleration exceeding a threshold for a set duration of time The trigger criteria can be combined into predefined patterns to refine event detection capabilities. In addition to the trigger criteria list above, individual axes or vector magnitudes can also be used for event detection. The trigger criteria, combinations of criteria, and patterns can also be used for false trigger rejection. For example, event detection can be implemented as linear or rotational acceleration exceeding a threshold, while false trigger rejection factors in a time duration or a particular pattern occurring or not occurring. In an example, a pattern can include a frequency content of a signal, presence or absence of a signal from components designed to detect changes in nearby electromagnetic properties, or signals to distinguish between a device mounted on the head, uniform or other body part versus a device that is not mounted. A signal to distinguish between a mounted device and a non-mounted device can include a signal generated by a connection in a headband (e.g., a connection that the USB A male connector can insert into). False trigger rejection can also examine the frequency of an impact to determine if it is within specific ranges consistent with an impact event. Detecting an impact detection device is in free fall can also be used as a false trigger rejection, as such an occurrence may indicate that the device was thrown in the air.

Algorithms to determine if device is mounted on a head (can tie into false trigger rejection algorithms), see discussion of FIG. 14 below for an example. Determining whether a device, such as the impact detection device 100, is actually being worn on an appropriate body part, such as the head, can be performed in numerous ways. In some examples, additional sensors can be included in the device, such as proximity sensors, capacitive sensors, infrared sensors, or some other type of thermal sensor. However, these examples require additional electronics and processing that can result in a more expensive and complicated device.

In an example, activity specific profiles can be developed to assist with outlier detection. Activity specific profiles can be compared against a user's average impacts to determine when a specific impact event is more severe than the typical hits the user experiences during a particular activity. Activity specific profiles can include national averages or other baseline type data to assist in comparing specific impact events. In certain examples, activity specific profiles can also be broken down by gender, age, body size, or other characteristics that may impact acceptable average impacts. Alerts can be generated when a particular impact event exceeds acceptable averages based on activity profile.

In an example, the impact detection devices can include power saving modes based upon user activity levels (detect walking gate, peak acceleration levels, frequency, etc.). Activity levels can be monitored by sampling acceleration over time. Metrics such as maximum acceleration, frequency of acceleration, and other characteristics can be used to determine when different sensors should be enabled. After long periods of inactivity the impact detection device can be placed into an ultra-low power mode.

In certain examples, it may be advantageous to translate measurements provided by an impact detection device to a person's center of gravity. Translation to center of gravity and head referenced axes can be accomplished by removing the rotational component of acceleration from the linear component, which depends on the radial distance from the center of mass of the object and the rotational acceleration. In examples where the impact detection device is mounted on a user's head, accurate measurement of how far the sensors are from the center of gravity of the head need to be determined. Methods for determining the distance from the impact detection device to the center of gravity can include using gender and age specific head size models or basic head measurements during an impact detection device set up procedure.

Figure 14:
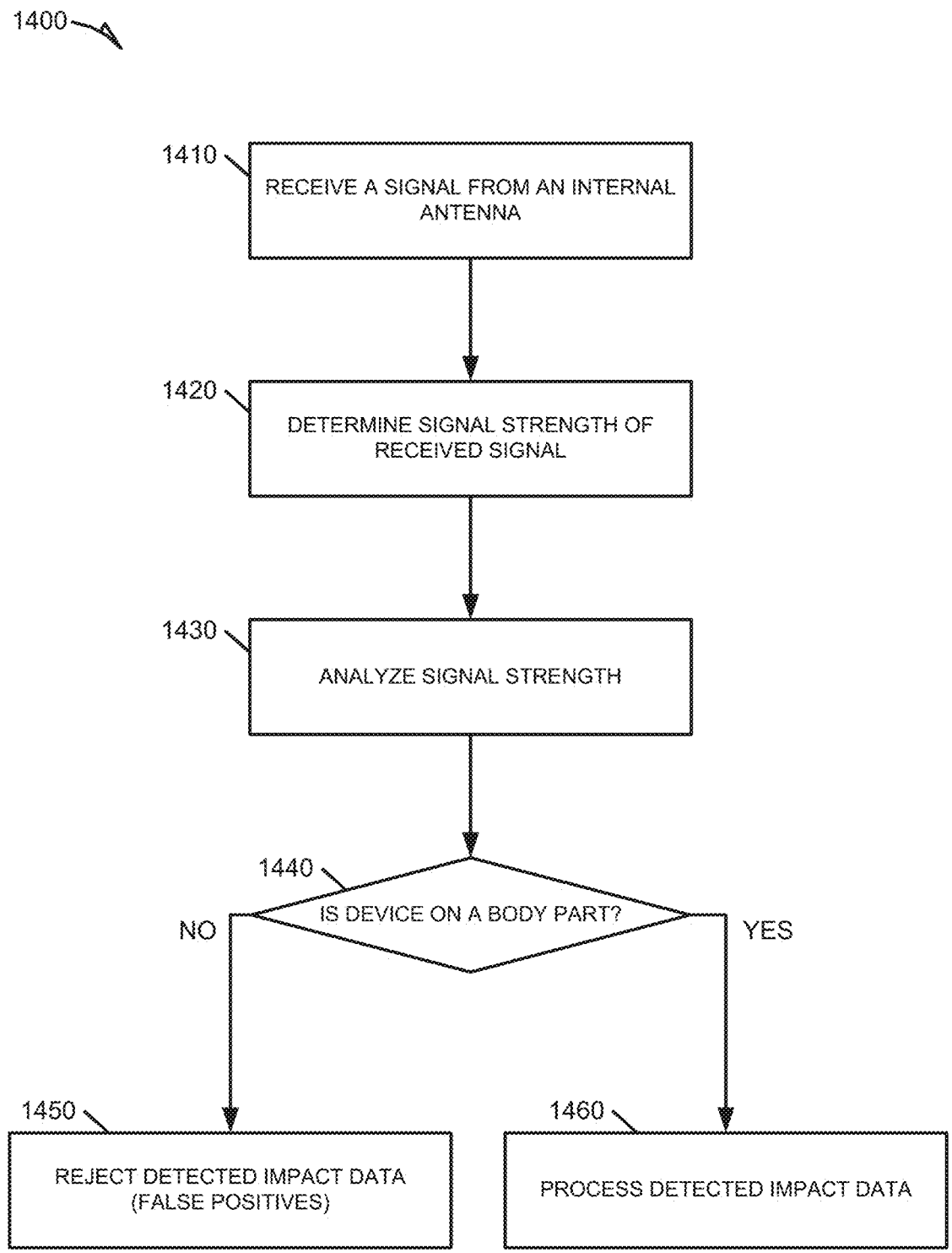
FIG. 14 is a flowchart illustrating an example method for rejecting false positive impact events detected by an impact detection device.

FIG. 14 is a flowchart illustrating an example method 1400 for rejecting false positive impact events detected by an impact detection device. In an example, the method 1400 can include operations such as: receiving a signal at 1410, determining a signal strength at 1420, analyzing signal strength at 1430, determining whether device is on a body part at 1440, rejecting impact data at 1450, and processing impact data at 1460. The method 1400 can include more or fewer operations than those depicted in FIG. 14 and the illustrated operations can be performed in a different order in some examples. Method 1400 is discussed and intended to be performed on the impact detection device 100; however, it is possible to perform the operations discussed in reference to method 1400 on a computing device external to the impact detection device 100.

In an example, an impact detection device, such as device 100, can include a secondary antenna and receiver for detecting signal strength of the primary antenna 116. The secondary antenna/receiver can be a full antenna/receiver added to the PCBA assembly. In another example, the secondary antenna/receiver can be a PCB trace with voltage monitoring via a discrete component (such as an analog to digital converter (ADC)). In other examples, the ADC can be integral to the microprocessor, which can monitor voltage. The secondary antenna and receiver can be used to detect the signal strength of the primary antenna, which can be tuned to provide an indication of whether the impact detection device 100 is being worn by the user. In an example, the primary antenna 116 can be tuned to provide maximum signal strength when the device 100 is in contact with a user's head (or other body part). When the device 100 is not in contact with a user's head, the primary antenna 116 becomes detuned and the signal strength (power output) drops. In an example, the secondary antenna and receiver can be tuned to only register a signal when the primary antenna 116 is producing a signal above a threshold level, with the threshold tuned to indicate contact with a body part.

In this example, the method 1400 can begin at 1410 with a secondary antenna/receiver component of the impact detection device 100 receiving a signal from the primary antenna 116. At 1420, the method 1400 can continue with the processor 104 determining signal strength of the signal measured on the secondary antenna, the signal received from the primary antenna 116. In another example, the secondary antenna/receiver component may be tuned to provide an essentially binary output, which would not require any processing by the processor 104. At 1430, the method 1400 can continue with the processor 104 analyzing the received signal strength to determine whether it exceeds a pre-defined threshold. At 1440, the method 1400 can continue with the processor 104 determining, based on analysis of the signal strength, whether the impact detection device 100 is in contact with a user's body part. In certain examples, the impact detection device 100 may be tuned for close proximity to a body part rather than direct contact. For example, the impact detection device 100 can be tuned to be worn attached to a helmet, to protective padding, or within a headband that puts some amount of padding between the user and the impact detection device 100. The pre-defined threshold can be tuned to accommodate different locations.

If at 1440, the processor 104 determines that the impact detection device 100 is in contact with (or close proximity to) a user's body part, the method 1400 can continue at 1460 with the processor 104 processing any detected impact data. However, if at 1440, the processor 104 determines that the impact detection device 100 is not in contact with (or close proximity to) a user's body part, the method 120 can continue at 1450 with the processor 104 rejecting any detected impact data, thus identifying false positives. In another example, the processor 104 can process detected impact data at 1450, but tag the data to indicate that it is likely a false positive.

Modules, Components and Logic

Certain embodiments are described herein as including logic or a number of components, modules, or mechanisms. Modules may constitute either software modules (e.g., code embodied on a machine-readable medium or in a transmission signal) or hardware modules. A hardware module is a tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or processors or processor-implemented modules. The performance of certain of the operations may be distributed among the one or more processors, not only residing within a single machine, but deployed across a number of machines. In some example embodiments, the processor or processors may be located in a single location (e.g., within an office environment or as a server farm), while in other embodiments the processors may be distributed across a number of locations. In certain examples, at least a portion of the processor-implemented operations can be performed on the sensor devices, such as sensor device 10.

The one or more processors may also operate to support performance of the relevant operations in a network-based (e.g. cloud) computing environment or as "software as a service" (SaaS). For example, at least some of the operations may be performed by a group of computers (as examples of machines including processors), with these operations being accessible via a network (e.g., the Internet) and via one or more appropriate interfaces (e.g., APIs).

Electronic Apparatus and System

Example embodiments may be implemented in digital electronic circuitry, or in computer hardware, firmware, software, or in combinations of them. Example embodiments may be implemented using a computer program product, for example, a computer program tangibly embodied in an information carrier, for example, in a machine-readable medium for execution by, or to control the operation of, data processing apparatus, for example, a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., a FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Example Machine Architecture and Machine-Readable Medium

Figure 15:
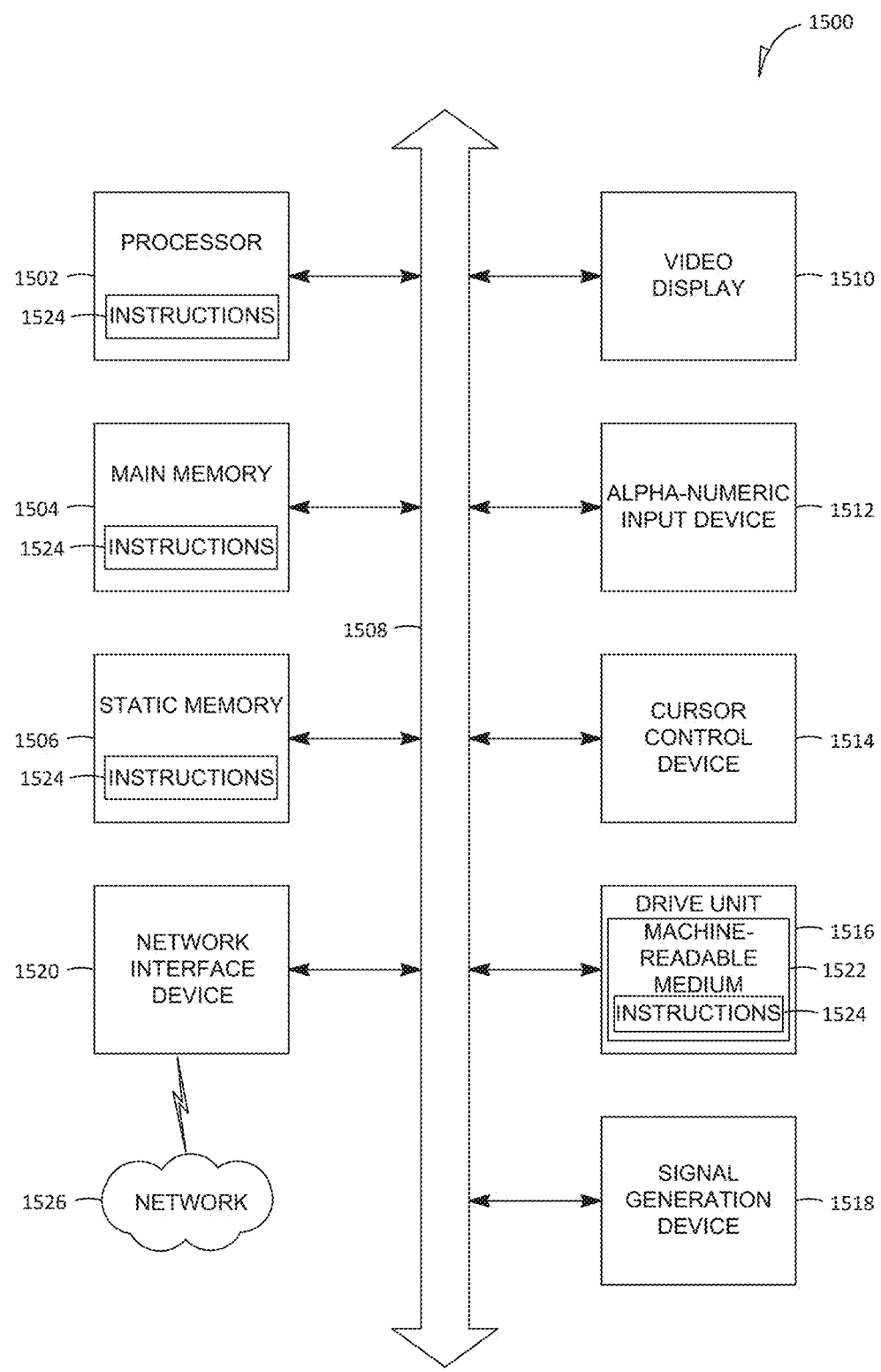
FIG. 15 is a diagrammatic representation of a machine in the example form of a computer system within which a set of instructions for causing the machine to perform any one or more of the methodologies discussed herein may be executed.

FIG. 15 is a block diagram of machine in the example form of a computer system 1500 within which instructions, for causing the machine to perform any one or more of the methodologies discussed herein, may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a PDA, a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1500 includes a processor 1502 (e.g., a central processing unit (CPU), a graphics processing unit (GPU) or both), a main memory 1504 and a static memory 1506, which communicate with each other via a bus 1508. The computer system 1500 may further include a video display unit 1510 (e.g., a liquid crystal display (LCD) or a cathode ray tube (CRT)). The computer system 1500 also includes an alphanumeric input device 1512 (e.g., a keyboard), a user interface (UI) navigation device 1514 (e.g., a mouse), a disk drive unit 1516, a signal generation device 1518 (e.g., a speaker) and a network interface device 1520.

Machine-Readable Medium

The disk drive unit 1516 includes a machine-readable medium 1522 on which is stored one or more sets of instructions and data structures (e.g., software) 1524 embodying or used by any one or more of the methodologies or functions described herein. The instructions 1524 may also reside, completely or at least partially, within the main memory 1504, static memory 1506, and/or within the processor 1502 during execution thereof by the computer system 1500, the main memory 1504 and the processor 1502 also constituting machine-readable media.

While the machine-readable medium 1522 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures used by or associated with such instructions. The term "machine-readable medium" shall accordingly be taken to include, but not be limited to, solid-state memories, and optical and magnetic media. Specific examples of machine-readable media include non-volatile memory, including by way of example, semiconductor memory devices (e.g., Erasable Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

Transmission Medium

The instructions 1524 may further be transmitted or received over a communications network 1526 using a transmission medium. The instructions 1524 may be transmitted using the network interface device 1520 and any one of a number of well-known transfer protocols (e.g., HTTP). Examples of communication networks include a LAN, a WAN, the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

Although the present invention has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense.

Although an embodiment has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be used and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended; that is, a system, device, article, or process that includes elements in addition to those listed after such a term in a claim are still deemed to fall within the scope of that claim. Moreover, in the following claims, the terms "first," "second," and "third," and so forth are used merely as labels, and are not intended to impose numerical requirements on their objects.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

The claimed invention includes:

1. A segmentally flexible package comprising:
   a rigid section encapsulating at least a portion of a circuit board populated with impact detection circuitry, the impact detect circuitry including:
   at least two sensors, the at least two sensors comprising a first accelerometer and at least one of a gyroscope and a second accelerometer;
   a communication circuit to transmit data captured by the at least two sensors to a computer device; and
   an integrated male connector comprising an extended portion of the circuit board with a plurality of connector pins disposed within a surface of the extended portion of the circuit board, wherein integrated male connector extends externally from a first side of the rigid section;
   a flexible section encapsulating a battery electrically connected to the impact detection circuitry, the flexible section including the battery mounted on a cantilevered portion moldable to a radius at least partially conforming to an external surface adjacent the segmentally flexible package; and
   a flex zone coupling the rigid section to the cantilevered portion of the flexible section, the flex zone in conjunction with the flexible section adapted to at least partially conform the segmentally flexible package to the external surface when the segmentally flexible package is held against the external surface by a carrier holding the segmentally flexible package.

2. The segmentally flexible package of claim 1, wherein the carrier holding the segmentally flexible package is clothing.

3. The segmentally flexible package of claim 1, wherein the carrier holding the segmentally flexible package is headwear.

4. The segmentally flexible package of claim 1, wherein the carrier holding the segmentally flexible package is a piece of sports equipment.

5. The segmentally flexible package of claim 1, wherein the external surface is associated with a body part of a user, wherein the carrier is worn externally on at least a portion of the body part, and wherein the segmentally flexible package at least partially conforms to a shape of an external surface of the body part.

6. The segmentally flexible package of claim 1, including charging circuitry coupled to the integrated male connector, the charging circuitry configured to charge the battery when the integrated male connector is connected to a power source.

7. The segmentally flexible package of claim 1, wherein the integrated male connector is an integrated male USB connector.

8. The segmentally flexible package of claim 1, wherein the rigid section, the flexible section, and the flex zone form a unified and continuous package including at least one contiguous surface, and wherein the at least one contiguous surface is adapted to be held against the external surface.

9. The segmentally flexible package of claim 1, wherein the flexible section is coupled to the rigid section at an initial angle.

10. The segmentally flexible package of claim 9, wherein the flex zone in conjunction with the flexible section enable deflection of the flexible section with respect to the rigid section from the initial angle to approximately a positive 10 degrees and a negative 20 degrees.

11. The segmentally flexible package of claim 1, wherein the at least two sensors comprise a first accelerometer and a gyroscope.

12. The segmentally flexible package of claim 1, wherein at least two sensors comprise a first accelerometer and a second accelerometer.

13. A device to detect impact to a body part of a user, the device comprising:
   at least two sensors, the at least two sensors comprising a first accelerometer and at least one of a gyroscope and a second accelerometer;
   a communication circuit to transmit data captured by the at least two sensors to a computer device; and
   an integrated connector extending from a circuit board holding the at least two sensors and the communication circuit;
   a battery electrically connected to the at least two sensors, the communication circuit, and the integrated male connector; and
   a segmentally flexible housing containing the at least two sensors, the communication circuit and the battery, the segmentally flexible housing including a first section and a second section connected via a flex zone and adapted to at least partially conform to an external surface of an object when compressed against the external surface, wherein the first section includes at least a portion of the circuit board and is substantially rigid, and wherein the second section is a cantilevered extension of the first section, includes the battery, and is moldable to a radius induced by the at least partial conformance to the external surface.

14. The device of claim 13, wherein the at least two sensors comprise a first accelerometer and a gyroscope.

15. The device of claim 13, wherein the at least two sensors comprise a first accelerometer and a second accelerometer.

16. The device of claim 13, including charging circuitry coupled to the connector, the charging circuitry configured to charge the battery when the connector is connected to a power source.

17. A sports accessory comprising:
   a head covering configured to be worn on a head of a user; and
   an impact detection device mounted to the head covering and located between at least a portion of the head covering and the head of the user, the impact detection device comprising:
   at least two sensors, the at least two sensors comprising a first accelerometer and at least one of a gyroscope and a second accelerometer;
   a communication circuit to transmit data captured by the at least two sensors to a computer device; and
   an integrated connector;
   a battery electrically connected to the at least two sensors, the communication circuit, and the integrated connector; and
   a segmentally flexible housing containing the at least two sensors, the communication circuit and the battery, the segmentally flexible housing including a first section and a second section connected via a flex zone and adapted to at least partially conform to the head of the user when compressed against the head by the head covering, wherein the first section includes at least a portion of the circuit board and is substantially rigid, and wherein the second section is a thin cantilevered extension of the first section adapted to receive the battery with the second section and the battery being moldable to a radius induced by the at least partial conformance to the head.

18. The sports accessory of claim 17, wherein the at least two sensors comprise a first accelerometer and a gyroscope.

19. The sports accessory of claim 17 wherein the at least two sensors comprise a first accelerometer and a second accelerometer.

20. The sports accessory of claim 17, including charging circuitry coupled to the connector, the charging circuitry configured to charge the battery when the connector is connected to a power source.

21. The sports accessory of claim 17 wherein the head covering is selected from a group of head coverings including:
   a headband;
   a skullcap;
   a piece of padding; and
   a helmet.

* * * * *